(12) United States Patent
Brandolini et al.

US012102607B2

(10) Patent No.: US 12,102,607 B2
(45) Date of Patent: Oct. 1, 2024

(54) C5aR INHIBITORS FOR USE IN THE TREATMENT OF CHEMOTHERAPY-INDUCED IATROGENIC PAIN

(71) Applicant: Dompe' Farmaceutici S.P.A., Milan (IT)

(72) Inventors: Laura Brandolini, L'Aquila (IT); Thiago Mattar Cunha, Sao Paulo (BR); Marcello Allegretti, L'Aquila (IT); Andrea Aramini, L'Aquila (IT); Gianluca Bianchini, L'Aquila (IT)

(73) Assignee: Dompe' Farmaceutici S.P.A., Milan (IT)

( * ) Notice: Subject to any disclaimer, the term of this patent is extended or adjusted under 35 U.S.C. 154(b) by 36 days.

(21) Appl. No.: 16/769,892

(22) PCT Filed: Dec. 11, 2018

(86) PCT No.: PCT/EP2018/084277
§ 371 (c)(1),
(2) Date: Jun. 4, 2020

(87) PCT Pub. No.: WO2019/115493
PCT Pub. Date: Jun. 20, 2019

(65) Prior Publication Data
US 2020/0397725 A1 Dec. 24, 2020

(30) Foreign Application Priority Data
Dec. 12, 2017 (EP) .................................... 17206813

(51) Int. Cl.
| | | |
|---|---|---|
| A61P 25/02 | (2006.01) | |
| A61K 31/145 | (2006.01) | |
| A61K 31/16 | (2006.01) | |
| A61K 31/166 | (2006.01) | |
| A61K 31/18 | (2006.01) | |
| A61K 31/337 | (2006.01) | |
| A61K 31/341 | (2006.01) | |
| A61K 31/381 | (2006.01) | |
| A61K 31/40 | (2006.01) | |
| A61K 31/421 | (2006.01) | |
| A61K 31/426 | (2006.01) | |
| A61K 31/4406 | (2006.01) | |
| A61K 31/445 | (2006.01) | |

(52) U.S. Cl.
CPC ............ *A61K 31/145* (2013.01); *A61K 31/16* (2013.01); *A61K 31/166* (2013.01); *A61K 31/18* (2013.01); *A61K 31/337* (2013.01); *A61K 31/341* (2013.01); *A61K 31/381* (2013.01); *A61K 31/40* (2013.01); *A61K 31/421* (2013.01); *A61K 31/426* (2013.01); *A61K 31/4406* (2013.01); *A61K 31/445* (2013.01); *A61P 25/02* (2018.01)

(58) Field of Classification Search
None
See application file for complete search history.

(56) References Cited

U.S. PATENT DOCUMENTS 8,133,911 B2 * 3/2012 Moriconi ................ A61P 21/00
548/326.5
2009/0124664 A1 5/2009 Allegretti
2010/0249198 A1 9/2010 Moriconi et al.

FOREIGN PATENT DOCUMENTS

| EA | 017250 B1 | 11/2012 |
|---|---|---|
| EP | 3192504 A1 | 7/2017 |
| WO | 2005090295 A2 | 9/2005 |
| WO | 2007060215 A2 | 5/2007 |
| WO | WO-2009/012482 A2 | 1/2009 |
| WO | 2009050258 A1 | 4/2009 |
| WO | 2017121838 A1 | 7/2017 |

OTHER PUBLICATIONS

Janeway CA Jr., Travers P., Walport M., et al. "The Complement System and Innate Immunity". Immunobiology: The Immune System in Health and Disease. 5th Edition, 2001. pp. 1-16. (Year: 2001).*
Akhilesh et al. "Combination Chemotherapy in Rodents: A Model for Chemotherapy-Induced Neuropathic Pain and Pharmacological Screening". Metabolic Brain Disease. 2024; 39:43-65. (Year: 2024).*
PCT International Search Report and Written Opinion dated Jun. 11, 2019 for Intl. App. No. PCT/EP2018/084277, from which the instant application is based, 19 pgs.
Xu, J., "Role of complement in paclitaxel-induced peripheral neuropathy," Abstract XPO055469048 (Oct. 22, 2017), 2 pgs.
Moriconi, A. et al., "Corrections-targeting the minor pocket of C5aR for the rational design of an oral allosteric inhibitor for inflammatory and neuropathic pain relief," Proceedings of the National Academy of Sciences, vol. 111, No. 52 (Dec. 30, 2014, 17 pgs.
Argyriou, A. et al., "Chemotherapy-Induced Peripheral Neurotoxicity (CIPN): An Update," Crit Rev Onol Hematol 2012; 82(1): 51-77.
Argyriou, A. et al., "Chemotherapy-induced peripheral neurotoxicity in adults, a comprehensive update of the literature," Cancer Manag Res. 2014; 6: 135-147.
Boyette-Davis, J. et al. "Intraepidermal nerve fiber loss corresponds to the development of Taxol-induced hyperalgesia and can be prevented by treatment with minocycline," Pain, 2011; 152: 308-313.
Brewer, J. et al., "Chemotherapy-induced peripheral neuropathy: current status and progress," Gynecologic Oncology 2016; 140:176-183.
Cascella, M. et al., "Chemotherapy-induced peripheral neuropathy: limitations in current prophylactic strategies and directions for future research," Current Medical Research and Opinion, 2017; 42:1-3.

(Continued)

*Primary Examiner* — Leslie A. Royds Draper
(74) *Attorney, Agent, or Firm* — Clark & Elbing LLP; Susan M. Michaud

(57) ABSTRACT

The present invention relates to C5aR inhibitor compounds, preferably C5aR noncompetitive allosteric inhibitors, useful in the treatment and/or prevention of chemotherapy-induced iatrogenic pain (CIIP).

11 Claims, 12 Drawing Sheets

(56) References Cited

OTHER PUBLICATIONS

Gerard, C et al., "C5a anaphylatoxin and its seven transmembranesegment receptor," Ann. Rev. Immunol., 1994, 12, 775-808.
Kumar, V. et al., "Cell-derived anaphylatoxins as key mediators of antibody-dependent type II autoimmunity in mice," J. Clin. Invest., 2006, 116(2), 512-520.
LaPointe, N. et al., "Effects of eribulin, vincristine, paclitaxel and ixabepilone on fast axonal transport and kinesin-1 driven microtubule gliding: Implications for chemotherapy-induced peripheral neuropathy," Neurotoxicology 2013; 37: 231-239.
Mielke, S. et al., "Peripheral neuropathy: A persisting challenge in paclitaxel-based regimes," Eur J Cancer 2006; 42:24-30.
Moriconi, A. et al., "Targeting the minor pocket of C5aR for the rational design of an oral allosteric inhibitor for inflammatory and neuropathic pain relief," PNAS, 2014, 111(47), 16937-16942.
Pachman, D. et al., "Chemotherapy-Induced Peripheral Neuropathy: Prevention and Treatment," Clin Pharmacol Ther 2011; 90: 377-387.
Polomano, R. et al., "A painful peripheral neuropathy in the rat produced by the chemotherapeutic drug, paclitaxel," Pain, 2001, 94, 293-304.
Shinde, S. et al., "Can pregabalin prevent paclitaxel-associated neuropathy?—An ACCRU pilot trial," Support Care Cancer, 2016, 24(2):547-553.
Wang, X. et al., "Discovering Cytokines as Targets for Chemotherapy-Induced Painful Peripheral Neuropathy," Cytokine 2012; 59 (1): 3-9.
Windebank, A. et al., "Chemotherapy-induced neuropathy," J Peripher Nerv Syst 2008; 13:27-46.
Tomassetti, M. et al., "Retention of stereochemistry in the microwave assisted synthesis of 1H-tetrazole bioisosteric moiety from chiral phenyl-acetic acid derivatives," Tetrahedron Letters, vol. 54, No. 46, Sep. 15, 2013, 6247-6250.
Peng, et al., Inflammation & Allergy—Drug Targets, 2009, 8, 236-246.
Warwick, C., "The role of complement component C5a in nociceptive sensitization"; Thesis (Doctor of Philosophy, Pharmacology), Graduate College of The University of Iowa, May 2017.
Choi, et al., Pain, 1994, 59, 369-376.
Office Action dated Nov. 16, 2023, for Russian Patent Application No. 2020122678, Brandolini et al., "C5AR Inhibitors for Use in the Treatment of Chemotherapy-Induced Iatrogenic Pain," filed Dec. 11, 2018 (English translation) (7 pages).
"W-54011 Data Sheet," MedChemExpress, <http://medchemexpress.com/W-54011.html>, retrieved Jan. 31, 2024 (2 pages).
Monk et al., "Function, structure and therapeutic potential of complement C5a receptors," Br J Pharmacol. 152(4):429-48 (Oct. 2007).
Sendler et al., "Complement Component 5 Mediates Development of Fibrosis, via Activation of Stellate Cells, in 2 Mouse Models of Chronic Pancreatitis," Gastroenterology. 149(3):765-76.e10 (Sep. 2015) (22 pages).
Seow et al., "Receptor residence time trumps drug-likeness and oral bioavailability in determining efficacy of complement C5a antagonists," Sci Rep. 6:24575 (Apr. 2016) (12 pages).
Seow, Vernon, Thesis: "Properties of the C5a Receptor on Human Macrophages," Bachelor of Science, The University of Queensland, 2014 (302 pages).
Sumichika et al., "Identification of a potent and orally active non-peptide C5a receptor antagonist," J Biol Chem. 277(51):49403-7 (Dec. 2002).
Waters et al., "Molecular characterization of the gerbil C5a receptor and identification of a transmembrane domain V amino acid that is crucial for small molecule antagonist interaction," J Biol Chem. 280(49):40617-23 (Dec. 2005).

\* cited by examiner

C5aR INHIBITORS FOR USE IN THE TREATMENT OF CHEMOTHERAPY-INDUCED IATROGENIC PAIN

RELATED APPLICATIONS

This application is a 35 U.S.C. 371 national stage filing from International Application No. PCT/EP2018/084277, filed Dec. 11, 2018, which claims priority to European Application No. 17206813.2, filed Dec. 12, 2017, the teachings of which are incorporated herein by reference.

TECHNICAL FIELD

The present invention relates to C5a receptor (C5aR) inhibitors for the prevention and treatment of chemotherapy-induced iatrogenic pain (CIIP) and in particular of allodynia associated thereof.

BACKGROUND ART

Different types of neurologic complications, including central neurotoxicity conditions ranging from minor cognitive deficits to encephalopathy with dementia or even coma, and peripheral neurotoxicity, may be associated with antineoplastic drug therapy, Iatrogenic pain is the most common neurological complication of cancer treatment, representing a set of symptoms ranging from minor, and temporary symptoms, to severe and permanent forms of polyneuropathy.

Because this kind of neurotoxicity is due to the administration of anticancer drugs it is commonly indicated as chemotherapy-induced iatrogenic pain (CIIP) (M. Cascella et al, CURRENT MEDICAL RESEARCH AND OPINION, 2017; 42:1-3). "Chemotherapy-induced iatrogenic pain (CIIP)" indicates a dose-limiting neurotoxic effect of chemotherapy to peripheral nerves. A number of different symptoms are associated with CIIP: hyperalgesia, allodynia, and spontaneous sensations such as burning, pain, numbness, spasm, and itching. In particular, although some of the symptoms induced by neurotoxicity of chemotherapeutic agents differs from patient to patient, a common sensory disruption leading to painful paresthesia is common to all affected patients.

CIIP occurs in about 60% of cancer patients (Windebank et al, J Peripher Nerv Syst 2008; 13:27-46) and can lead to dose limitation or even discontinuation of treatment, therefore ultimately affecting survival of the patient (Mielke et al, Eur J Cancer 2006; 42:24-30).

In particular, the chemotherapeutic agents that are most commonly associated with the onset of peripheral pain include platinum-based drugs, for example cisplatin, carboplatin and oxaliplatin; taxanes, for example paclitaxel, cabazitaxel and docetaxel; epothilones, for example ixabepilone; plant alkaloids, for example vinblastine, vincristine, vinorelbine and etoposide; thalidomide, lenalidomide and pomalidomide; carfilzomib and bortezomib; eribulin (Brewer et al, Gynecologic Oncology 2016; 140:176-83).

Although a variety of neuroprotective approaches have been investigated in both experimental studies and clinical trials, there is at the moment no available preventive strategy or effective treatment for CIIP, also because their etiology have not yet been fully elucidated.

Multiple mechanisms have been proposed to underlie the development and maintenance of pain.

Some evidence suggests that inflammatory cytokines/chemokines and in particular TNF-α, IL-1β, IL-6 and CCL2 may have a role in chemotherapeutic agent-induced pain symptoms in CIIP (Wang et al, Cytokine 2012; 59 (1): 3-9). However, strong evidence also suggests a direct effect of chemotherapeutic drugs on sensory neurons (Argyriou et al, Crit Rev Onol Hematol 2012; 82(1): 51-77, Boyette-Davis et al, Pain, 2011; 152: 308-13; Pachman et al, Clin Pharmacol Ther 2011; 90: 377-387). In particular, it has been established that most chemotherapeutic drugs can easily penetrate the blood-nerve-barrier (BNB) and bind to the dorsal root ganglia (DRG) and peripheral axons (Wang et al, see above). There is also evidence that these drugs then directly damage the structure of the DRG cells and peripheral nerves with the consequent degeneration of sensory fibers and loss of small nerve fibers in the epidermal layer (Argyriou et al, Cancer Manag Res. 2014; 6:135-147).

At the cellular level neurotoxic chemotherapeutic agents damage microtubules, interfere with microtubule-based axonal transport (LaPointe et al, Neurotoxicology 2013; 37: 231-9), affect microtubule dynamics, by inducing α-tubulin acetylation, interrupt mitochondrial function, or directly target DNA. Nerve biopsies from experimental animals and patients treated with paclitaxel, oxaliplatin or vincristine show identical morphological changes, suggesting an underlying common pathogenetic mechanism.

The C5a peptide fragment of the complement has been defined as the "complete" pro-inflammatory mediator due to its chemotactic and inflammatory activity. In fact, other inflammatory mediators such as selected chemokines (IL-8, MCP-I and RANTES, for example) are highly selective towards self-attracted cells, while others, such as histamine and bradykinin, are only weak chemotactic agents. Convincing evidences support the involvement of C5a, in vivo, in several pathological conditions including ischemia/reperfusion, autoimmune dermatitis, membrane-proliferative idiopathic glomerulonephritis, airway irresponsiveness and chronic inflammatory diseases, ARDS and CODP, Alzheimer's disease, juvenile rheumatoid arthritis (N. P. Gerard, Ann. Rev. Immunol., 12, 755, 1994). The pathological significance of C5a and its selective receptor C5aR in the development of diseases related to antibody-dependent type II autoimmunity has been also investigated, specifically in the insurgence of autoimmune haemolytic anaemia (AIHA), a disease characterized by the production of antibodies directed against self red blood cells (RBCs) that causes haemolysis. AIHA is a fairly uncommon disorder, with estimates of incidence at 1-3 cases/100.000/year. A crucial role of C5a in IgG-dependent AIHA, independent from the chemotactic function of this anaphylotoxin, has been identified in experimental animal models (V. Kumar, J. Clin. Invest., 116(2), 512, 2006). In fact, it has been observed that mice lacking C5aR are partially resistant to this IgG autoantibody-induced disease model and a cross-talk of C5aR with activating Fcγ receptors, specifically on liver macrophages, has been identified through the observation that, upon administration of anti-erythrocyte antibodies, upregulation of activating FcγRs on Kupfer cells was absent in C5aR-deficient mice; parallely, in mice deficient in FcγRs, C5 and C5a production was abolished. This is the first evidence of a previously unidentified FcγR-mediated C5a-generating pathway, suggesting the role of C5a in the development of antibody-dependent autoimmune diseases and potential therapeutic benefits of C5a and/or C5aR blockade in AIHA related to type II autoimmune injury.

WO2007/060215 discloses (R)-arylalkylamino derivatives and their use in the treatment of diseases that involve C5a induced human PMNs chemotaxis such as sepsis, psoriasis, bullous pemphigoid, rheumatoid arthritis, ulcerative colitis, acute respiratory distress syndrome, idiopathic fibrosis, cystic fibrosis, chronic obstructive pulmonary disease, glomerulonephritis and in the prevention and the treatment of injury caused by ischemia and reperfusion.

WO2009/050258 discloses (R)-4-(heteroaryl)phenylethyl compounds and their use in the treatment of diseases that involve C5a induced human PMNs chemotaxis, such as autoimmune hemolytic anemia (AIHA), psoriasis, bullous pemphigoid, rheumatoid arthritis, ulcerative colitis, acute respiratory distress syndrome, idiopathic fibrosis, glomerulonephritis and in the prevention and treatment of injury caused by ischemia and reperfusion.

The published paper A. Moriconi et al, PNAS, 111(47), 16937-16942, 2014 discloses the effect of a novel potent allosteric inhibitor of the C5a anaphylatoxin receptor (C5aR) in reducing mechanical hyperalgesia in several models of acute and chronic inflammatory pain and in the SNI-induced neuropathic pain model in mice, which use tibial and peroneal axotomy to induce chronic allodynia on the injured hind paw. Procedures followed to induce neuropathy and specific characteristics of a particular model are crucial to understand the underlying mechanisms and formulate effective management therapy. Especially in the context of chemotherapy-induced iatrogenic pain, the efficacy of a therapeutic approach appears to be strictly correlated to the identification of specific targets. Corroborating this hypothesis, scientific evidence do not support the use of agents effective in treating general pain in the management of chemotherapy-induced iatrogenic pain (Shinde S S et al, Support Care Cancer, 24(2):547-553, 2016).

Differently from the traumatic injury originally described in the published paper A. Moriconi et al, PNAS, 111(47), 16937-16942, 2014, the current data referred to a validated model of neurotoxicity induced by chemotherapy-specific mechanisms, in particular to taxanes (Polomano R C et al, Pain, 94, 293, 2001). Taxanes, especially paclitaxel, interfere with dynamic physiological reorganization of microtubules network, which is essential for cell vital functions, and induce oxidative stress. C5a and its cell membrane receptor C5aR, has been associated with acute, inflammatory and neuropathic pain states; however, the role of C5a/C5aR in chemotherapy-induced iatrogenic pain has not yet been investigated.

SUMMARY OF THE INVENTION

The present inventors have surprisingly found that inhibition of C5aR is able to reduce or prevent the occurrence of symptoms associated with toxicity of systemic anticancer chemotherapy leading to chemotherapy-induced iatrogenic pain (CIIP).

Moreover, C5aR inhibitors useful in the prevention and/or treatment of chemotherapy-induced iatrogenic pain do not interfere in any way with the activity of the chemotherapeutic agent.

Accordingly, a first object of the present invention is a C5aR inhibitor, preferably a C5aR noncompetitive allosteric inhibitor, for use in the prevention and/or treatment of chemotherapy-induced iatrogenic pain.

The second object of the present invention is the use of a C5aR inhibitor for the preparation of a medicament for the treatment and/or prevention of chemotherapy-induced iatrogenic pain.

The third object of the present invention is a method for the prevention and/or treatment of CIIP comprising the step of administering to a subject in need thereof a therapeutically effective amount of said C5aR inhibitor.

The fourth object of the invention is a pharmaceutical composition for the prevention and/or treatment of CIIP comprising a C5aR inhibitor according to the invention and pharmaceutically acceptable excipients.

DESCRIPTION OF THE FIGURES

FIG. 7. α-tubulin levels under challenge with C5a alone or in combination with DF3966Y. Data are mean±SD of 3 different experiments. **p<0.01 vs untreated cells, UT; #p<0.05 vs C5a.

FIG. 9. Treatment C) Representative trace of electrophysiological recordings in DRG cells challenged with C5a;

Treatment D) Representative trace of electrophysiological recordings in DRG cells challenged with C5a+DF3966Y.

Figure 10:
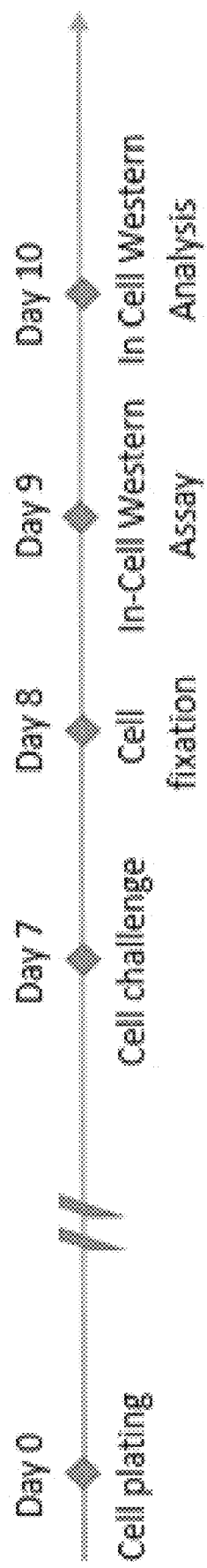

FIG. 10. Schematic showing experimental challenge scheme for isolated dorsal root ganglion neurons.

DETAILED DESCRIPTION OF THE INVENTION

As it will be disclosed in details in the Experimental Section, the present inventors have found that molecules acting as inhibitors of C5aR activity have therapeutic efficacy in animal models of iatrogenic pain-induced by Paclitaxel. Furthermore, the present inventors have also found that C5aR inhibition is able to counteract the activity of the chemotherapeutic agent on the cytoskeleton components and organization that contributes to its neurotoxic effects.

Accordingly, a first object of the present invention is C5aR inhibitor for use in the treatment and/or prevention of chemotherapy-induced iatrogenic pain (CIIP).

According to a preferred embodiment, said C5aR inhibitor is for use in the prevention and/or treatment of allodynia associated to chemotherapy-induced iatrogenic pain (CIIP).

The term "C5aR inhibitor" according to the present application refers to any compound able to inhibit, partially or totally, the biological activity of C5a and/or C5aR. Such a compound can act by decreasing the expression or activity of C5a or by inhibiting the triggering of the intracellular signaling activated by the C5a receptors. It is preferred that said C5a inhibitor is able to inhibit at least 50%, preferably at least 60%, of the chemotaxis induced by C5a in PMNs at a concentration equal or below 500 nM, preferably below 100 nM.

The second object of the present invention is the use of a C5aR inhibitor for the preparation of a medicament for the treatment and/or prevention of chemotherapy-induced iatrogenic pain (CIIP).

According to a preferred embodiment of the present invention, said medicament is for the treatment and/or prevention of allodynia associated to chemotherapy-induced iatrogenic pain.

The third object of the present invention is a method for the treatment and/or prevention of chemotherapy-induced iatrogenic pain, comprising the step of administering to the subject in need thereof, a therapeutically effective amount of an C5aR inhibitor, as defined above.

According to a preferred embodiment of the present invention, said method is for the treatment and/or prevention of allodynia associated to chemotherapy-induced iatrogenic pain.

As used herein, a "therapeutically effective amount" refers to an amount sufficient to achieve treatment or prevention of the disease. Determination of the effective amounts is well within the capability of those skilled in the art based upon the achievement of a desired effect. An effective amount will depend on factors including, but not limited to, the weight of a subject and/or the degree of the disease or unwanted condition from which a subject suffers. The terms "treatment" and "prevention" as used herein refer to the eradication/amelioration or prevention/delay in onset, respectively, of the disorder being treated or of one or more of the symptoms associated thereof, notwithstanding the fact that the patient may still be afflicted with the underlying disorder.

The fourth object of the present invention is a pharmaceutical composition comprising a C5aR inhibitor, for use in the treatment and/or prevention of chemotherapy-induced iatrogenic pain (CIIP) in association with pharmaceutically suitable excipients.

According to a preferred embodiment of the present invention, said pharmaceutical composition is for the treatment and/or prevention of allodynia associated to chemotherapy-induced iatrogenic pain.

According to a preferred embodiment, the C5aR inhibitor of all the objects of the present invention is a noncompetitive allosteric inhibitor of C5a receptor.

By "noncompetitive allosteric inhibitor of C5a receptor" according to the present invention it is meant a compound that shows the interaction with C5a receptors in an allosteric site, located in the TM region, inhibits intracellular signal transduction events activated by the agonist binding, without affecting any binding of endogen ligand C5a on its receptor.

Preferred C5aR inhibitors according to the invention are selected from (R)-arylalkylamino derivatives, (R)-4-(heteroaryl)phenylethyl compounds and their pharmaceutically acceptable salts.

Among the above compounds, said (R)-arylalkylamino derivative is preferably a compound of formula (I):

(I)

or a pharmaceutically acceptable salt thereof, wherein
R is selected from:
2-thiazolyl or 2-oxazolyl, unsubstituted or substituted by a group selected from methyl, tert-butyl or trifluoromethyl group;
C(Ra)=N-W wherein W is linear or branched C1-C4 alkyl,
CORa, SORa, SO$_2$Ra, PORa, PO$_2$Ra,
wherein
Ra is selected from
C$_1$-C$_5$-alkyl, C$_3$-C$_6$-cycloalkyl, C$_2$-C$_5$-alkenyl, unsubstituted or substituted phenyl with a group selected from halogen, C$_1$-C$_4$-alkyl, C$_1$-C$_4$-alkoxy, halo-C$_1$-C$_4$-alkoxy, hydroxy, C$_1$-C$_4$-acyloxy, phenoxy, cyano, nitro, amino;
a heteroaryl group selected from pyridine, pyrimidine, pyrrole, thiophene, furane, indole, thiazole, oxazole, such heteroaryl being unsubstituted or substituted with a group selected from halogen, C$_1$-C$_4$-alkyl, C$_1$-C$_4$-alkoxy, halo-C$_1$-C$_4$-alkoxy, hydroxy, C$_1$-C$_4$-acyloxy, phenoxy, cyano, nitro, amino;
a α or β carboxyalkyl residue consisting of straight or branched C$_1$-C$_6$-alkyl, C$_3$-C$_6$-cycloalkyl, C$_2$-C$_6$-alkenyl, C$_1$-C$_6$-phenylalkyl, optionally substituted with a further carboxy (COOH) group;
an ω-aminoalkylamino group of formula II:

(II)

wherein
X represents:

linear or branched $C_1$-$C_6$ alkylene, $C_4$-$C_6$ alkenylene, $C_4$-$C_6$ alkynylene, optionally substituted by a $CO_2R4$ group or by a $CONHR5$ group, wherein R4 represents hydrogen or a linear or branched $C_1$-$C_6$ alkyl group or a linear or branched $C_2$-$C_6$ alkenyl group, wherein R5 represents hydrogen, linear or branched $C_2$-$C_6$ alkyl or an OR4 group, R4 being defined as above;

a $(CH_2)_m$—B—$(CH_2)_n$, group, optionally substituted by a $CO2R4$ or $CONHR5$ group, as defined above, wherein B is an oxygen, or sulfur atom, or nitrogen atom optionally substituted by a $C_1$-$C_4$ alkyl group, m is zero or an integer from 2 to 3 and n is an integer from 2 to 3, or B is a CO, SO or CONH group, m is an integer from 1 to 3 and n is an integer from 2 to 3;

or X together with the nitrogen atom to which it is bound and with the R2 group forms a nitrogen containing 3-7 membered heterocyclic, monocyclic or polycyclic ring, and R3 represents hydrogen, $C_1$-$C_4$ alkyl, $C_1$-$C_4$ acyl, unsubstituted or substituted phenyl with a group selected from halogen, $C_1$-$C_4$-alkyl, $C_1$-$C_4$-alkoxy, hydroxy, $C_1$-$C_4$- acyloxy, phenoxy, cyano, nitro, amino;

R2 and R3 are independently:

hydrogen, linear or branched $C_1$-$C_6$ alkyl, optionally interrupted by an oxygen or sulfur atom, a $C_3$-$C_7$ cycloalkyl, $C_3$-$C_6$ alkenyl, $C_3$-$C_6$-alkynyl, aryl-$C_1$-$C_3$-alkyl, hydroxy-$C_2$-$C_3$-alkyl group;

or R2 and R3 together with the N atom to which they are bound, form a 3-7 membered nitrogen heteroryclic ring of formula (III)

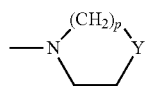

(III)

wherein

Y represents:

a single bond, $CH_2$, O, S, or a N—R6 group, where R6 represents hydrogen, $C_1$-$C_4$ alkyl, $C_1$-$C_4$ acyl, unsubstituted or substituted phenyl with a group selected from halogen, $C_1$-$C_4$-alkyl, $C_1$-$C_4$- alkoxy, hydroxy, $C_1$-$C_4$-acyloxy, phenoxy, cyano, nitro, amino, and p represents an integer from 0 to 3;

a residue of formula $SO_2R7$ wherein R7 is $C_1$-$C_6$-alkyl, $C_3$-$C_6$-cycloalkyl, $C_2$-$C_6$-alkenyl, aryl and heteroaryl;

R1 is linear or branched $C_1$-$C_5$ alkyl, $C_3$-$C_5$ cycloalkyl;

Ar is a phenyl group unsubstituted or substituted by one or more groups independently selected from halogen, $C_1$-$C_4$-alkyl, $C_1$-$C_4$-alkoxy, hydroxy, $C_1$-$C_4$-acyloxy, phenoxy, cyano, nitro, amino, $C_1$-$C_4$-acylamino, halo-$C_1$-$C_3$- alkyl, halo-$C_1$-$C_3$-alkoxy, benzoyl, heteroaryl carbonyl, heteroaryl, linear or branched $C_1$-$C_8$-alkanesulfonate, linear or branched $C_1$-$C_5$-alkanesulfonamides, linear or branched $C_1$-$C_8$ alkyl sulfonylmethyl;

or Ar is a heteroaryl ring selected from pyridine, pyrrole, thiophene, furan, indole.

Among the above compounds, particularly preferred are compounds of said formula (1) or pharmaceutically acceptable salts thereof, wherein:

R is selected from:

2-thiazolyl or 2-oxazolyl, unsubstituted or substituted by a group selected from methyl, tert-butyl or trifluoromethyl group;

C(Ra)=N-W wherein W is linear or branched $C_1$-$C_4$ alkyl,

CORa, SORa or $SO_2Ra$, wherein Ra is as defined above;

Ar is selected from:

3'-benzoylphenyl, 3'-(4-chloro-benzoyl)-phenyl, 3'-(4-methyl-benzoyl)-phenyl, 3'-acetyl-phenyl, 3'-propionyl-phenyl, 3'-isobutanoyl-phenyl, 4'-isobutyl-phenyl, 4'-trifluoromethanesulfonyloxy-phenyl, 4'-benzenesulfonyloxy-phenyl, 4'-trifluoromethanesulfonylamino-phenyl, 4'-benzenesulfonylamino-phenyl, 4'-benzenesulfonylmethyl-phenyl, 4'-acetoxyphenyl, 4'-propionyloxy-phenyl, 4'-benzoyloxy-phenyl, 4'-acetylamino-phenyl, 4'-propionylamino-phenyl, 4'-benzoylamino-phenyl, 3'-(furan-2-carbonyl)-phenyl, 3'-(benzofuran-2-carbonyl)-phenyl, 3'-(thiophen-2-carbonyl)-phenyl, 3'-(pyridine-2-carbonyl)-phenyl, 3'-(thiazole-2-carbonyl)-phenyl, 3'-(oxazole-2-carbonyl)-phenyl, 3'-(2-furyl)-phenyl, 3'-(2-oxazolyl)-phenyl, 3'-(3-isoxazolyl)-phenyl, 3'-(2-benzoxazolyl)-phenyl, 3'-(3-benzoisoxazolyl)-phenyl, 3'-(2-thiazolyl)-phenyl, 3'-(2-pyridyl)-phenyl, 3'-(2-thiophenyl)-phenyl;

or Ar is a heteroaryl ring selected from pyridine, pyrrole, thiophene, furan or indole. Among the above compounds, particularly preferred are also compounds of said formula (I) or pharmaceutically acceptable salts thereof, wherein:

R is 2-thiazolyl, unsubstituted or substituted by a group selected from methyl or trifluoromethyl group;

CORa, $SO_2Ra$, SORa;

wherein

Ra is selected from:

$C_1$-$C_5$-alkyl, $C_3$-$C_5$-cycloalkyl;

phenyl, 2-pyridyl, 2-thiazolyl, 2-furyl, 2-pyrrolyl, 2-thiofenyl, 2-indolyl groups;

a carboxylalkyl group consisting of straight or branched $C_1$-$C_5$-alkyl, $C_1$-$C_6$-phenylalkyl group;

an ω-alkylamino group of formula II,

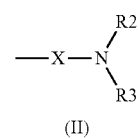

(II)

wherein

X represents:

linear or branched $C_1$-$C_6$ alkylene, $C_4$-$C_6$ alkenylene, $C_4$-$C_6$ alkynylene; or X together with the nitrogen atom to which it is bound and with the R2 group forms a nitrogen containing 3-7 membered heterocyclic monocyclic ring and R3 represents hydrogen or $C_1$-$C_4$ alkyl;

R2 and R3 are independently hydrogen, linear or branched $C_1$-$C_6$ alkyl, $C_3$-$C_7$ cycloalkyl, $C_3$-$C_6$ alkenyl, $C_3$-$C_6$-alkynyl;

or R2 and R3 together with the N atom to which they are bound, form a 4-6 membered nitrogen containing heterocyclic ring of formula (III)

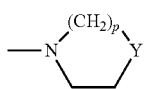

(III)

wherein Y represents CH$_2$, O, S, or a N—R6 group, where R6 represents hydrogen, C$_1$-C$_4$ alkyl, C$_1$-C$_4$ acyl, and p represents an integer from 0 to 2;

R1 is methyl;

Ar is selected from:

3'-benzoylphenyl, 3'-(4-chloro-benzoyl)-phenyl, 3'-(4-methyl-benzoyl)-phenyl, 3'-acetyl-phenyl, 3'-propionyl-phenyl, 3'-isobutanoyl-phenyl, 4'-isobutyl-phenyl, 4'-trifluoromethanesulfonyloxy-phenyl, 4'-benzenesulfonyloxy-phenyl, 4'-trifluoromethanesulfonylamino-phenyl, 4'-benzenesulfonylamino-phenyl, 4'-benzenesulfonylmethyl-phenyl, 4'-acetoxyphenyl, 4'-propionyloxy-phenyl, 4'-benzoyloxy-phenyl, 4'-acetylamino-phenyl, 4'-propionylamino-phenyl, 4'-benzoylamino-phenyl; 3'-(furan-2-carbonyl)-phenyl; 3'-(benzofuran-2-carbonyl)-phenyl; 3'-(thiophen-2-carbonyl)-phenyl; 3'-(pyridine-2-carbonyl)-phenyl, 3'-(thiazole-2-carbonyl)-phenyl, 3'-(oxazole-2-carbonyl)-phenyl; 3'-(2-furyl)-phenyl, 3'-(2-oxazolyl)-phenyl, 3'-(3-isoxazolyl)-phenyl, 3'-(2-benzoxazolyl)-phenyl, 3'-(3-benzoisoxazolyl)-phenyl, 3'-(2-thiazolyl)-phenyl, 3'-(2-pyridyl)-phenyl, 3'-(2-thiophenyl)-phenyl.

Among the above compounds, particularly preferred are also compounds of said formula (I) or pharmaceutically acceptable salts thereof, wherein wherein R is 2-thiazolyl, unsubstituted or substituted by a group selected from methyl or trifluoromethyl;

CORa, SO$_2$Ra wherein

Ra is selected from:

C$_1$-C$_5$-alkyl, C$_3$-C$_5$-cycloalkyl;

phenyl, 2-pyridyl, 2-furyl, 2-thiophenyl groups;

a group of formula II,

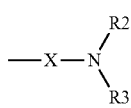

(II)

wherein

X represents:

linear or branched C$_1$-C$_6$ alkylene,

R2 and R3 together with the N atom to which they are bound, form a 4-6 membered nitrogen containing heterocyclic ring of formula (III)

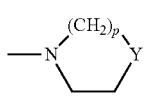

(III)

wherein Y represents CH$_2$, and p represents an integer from 0 to 2;

R1 is methyl;

Ar is selected from:

3'-benzoylphenyl, 3'-(4-chloro-benzoyl)-phenyl, 3'-(4-methyl-benzoyl)-phenyl,

4'-trifluoromethanesulfonyloxy-phenyl, 4'-benzenesulfonyloxy-phenyl, 3'-(furan-2-carbonyl)-phenyl.

Particularly preferred are compounds of formula (I) according to the invention selected from:

4-{(1 R)-1-[(phenylsulfonyl)amino]ethyl}phenyl trifluoromethanesulfonate

N-[(1R)-1-(3-benzoylphenyl)ethyl]benzenesulfonamide

4-{(1R)-1-[(pyridine-3-ylsulfonyl)amino]ethyl}phenyltrifluoromethanesulfonate

N-[(1R)-1-(3-benzoylphenyl)ethyl]methanesulfonamide

N-{(1R)-1-[3-(2-furoyl)phenyl]ethyl)thiophene-2-sulfonamide

N-{(1R)-1-[3-(2-furoyl)phenyl]ethyl}methanesulfonamide

4-{(1R)-1-[(thien-2-ylsulfonyl)amino]ethyl}phenyl trifluoromethanesulfonate

N-[(1R)-1-(3-benzoylphenyl)ethyl]thiophene-2-sulfonamide

N-[(1R)-1-(3-benzoylphenyl)ethyl]-3-pyrrolidin-1-ylpropane-1-sulfonamide methyl 5-({[(1R)-1-(3-benzoylphenyl)ethyl]amino}sulfonyl)-2-furoate 5-({[(1R)-1-(3-benzoylphenyl)ethyl]amino}sulfonyl)-2-furoic acid 4-{(1R)-2-methyl-1-[(methylsulfonyl)amino]propyl}phenyltrifluoromethanesulfonate N-((1R)-1-{4-[1-methyl-1-(phenylsulfonyl)ethyl]phenyl}ethyl)methanesulfonamide 4-[(1R)-1-(isobutyrylamino)ethyl]phenyltrifluoromethanesulfonate 4-{[(1R)-1-(pyridine-3-ylcarbonyl)amino]ethyl]}phenyltrifluoromethanesulfonate N-[(1R)-1-(3-benzoylphenyl)ethyl]benzamide N-[(1R)-1-(3-benzoylphenyl)ethyl]-2-furamide N-[(1R)-1-(3-benzoylphenyl)ethyl]cyclobutanecarboxamide N-[(1R)-1-(4-trifluoromethanesulfonyloxy)phenylethyl]-4-piperidin-1-ylbutanamide 4-{(1R)-1-[(4-pyrrolidin-1-ylbutanoyl)amino]ethyl]}phenyl trifluoromethanesulfonate 3-{(1R)-1-[4-(4-trifluoromethyl-1,3-thiazol-2-yl)amino]ethyl}phenyl) (phenyl)methanone.

Particularly preferred are compounds of formula (I) according to the invention selected from N-[(1R)-1-(4-trifluoromethanesulfonyloxy)phenylethyl]-4-piperidin-1-ylbutanamide (herein indicated also as DF2593Y) and pharmaceutically acceptable salts thereof, preferably its chloride salt (herein indicated also as DF2593A). Compounds of formula (I) are disclosed in WO2007/060215, which also discloses their method of synthesis, their activity as C5aR inhibitors as well as their use in the treatment of diseases that involve C5a induced human PMNs chemotaxis such as sepsis, psoriasis, bullous pemphigoid, rheumatoid arthritis, ulcerative colitis, acute respiratory distress syndrome, idiopathic fibrosis, cystic fibrosis, chronic obstructive pulmonary disease, glomerulonephritis and in the prevention and the treatment of injury caused by ischemia and reperfusion.

Among the above C5aR inhibitors, said (R)-4-(heteroaryl) phenylethyl compound is preferably a compound of formula (II):

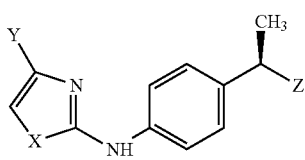

(II)

or a pharmaceutically acceptable salt thereof,
wherein
X is a heteroatom selected from
S, O and N
Y is H or a residue selected from the group consisting of:
halogen, linear or branched $C_1$-$C_4$-alkyl, $C_2$-$C_4$-alkenyl, $C_1$-$C_4$-alkoxy, hydroxy,—COOH, $C_1$-$C_4$-acyloxy, phenoxy, cyano, nitro,—$NH_2$, $C_1$-$C_4$-acylamino, halo-$C_1$-$C_3$-alkyl, benzoyl, linear or branched $C_1$-$C_8$-alkanesulfonate, linear or branched $C_1$-$C_8$-alkanesulfonamides, linear or branched $C_1$-$C_8$-akyl sulfonylmethyl;
Z is an heteroaryl ring selected from the group consisting of:
unsubstituted tetrazole and
triazole, pyrazole, oxazole, thiazole, isooxazole, isothiazole, thiadiazole and oxadiazole substituted by one hydroxy group and optionally further substituted by one or more groups selected from the group consisting of halogen, linear or branched $C_1$-$C_4$-alkyl, $C_2$-$C_4$-alkenyl, $C_1$-$C_4$-akylamino, $C_1$-$C_4$-alkoxy, $C_1$-$C_4$-alkylthio, $C_1$-$C_4$-acyloxy, cyano, nitro, $NH_2$, $C_1$-$C_4$-acylamino, halo-$C_1$-$C_3$-alkyl, halo-$C_1$-$C_3$-alkoxy, linear or branched $C_1$-$C_5$-alkanesulfonate and linear or branched $C_1$-$C$-alkanesulfonamides.

Among the above compounds, preferred are compounds of formula (II) or a pharmaceutically acceptable salts thereof, wherein:
X is a heteroatom selected from
S and O
Y is H or a residue selected from the group consisting of:
halogen, linear or branched $C_1$-$C_4$-alkyl and halo-$C_1$-$C_3$-alkyl; preferably selected from the group consisting of trifluoromethyl, chlorine, methyl and tert-butyl;
Z is an heteroaryl ring selected from the group consisting of:
unsubstituted tetrazole and triazole, pyrazole, isooxazole, isothiazole, thiadiazole and oxadiazole substituted by one hydroxy group and optionally further substituted by one or more groups selected from the group consisting of halogen, linear or branched $C_1$-$C_4$-alkyl, $C_1$-$C_4$-alkylthio and halo-$C_1$-$C_3$-alkyl; preferably selected from the group consisting of methyl, trifluoromethyl and chlorine.

Particularly preferred compounds of formula (II) according to the invention are selected from:
N-{4-[(1R)-1-(1H-tetrazol-5-yl)ethyl]phenyl}-4-(trifluoromethyl)-1,3-thiazol-2-amine;
4-methyl-N-{4-[(1R)-1-(1H-tetrazol-5-yl)ethyl]phenyl}-1, 3-thiazol-2-amine;
4-tert-butyl-N-{4-[(1R)-1-(1H-tetrazol-5-yl)ethyl]phenyl}-1,3-thiazol-2-amine;
N-{4-[(1R)-1-(1H-tetrazol-5-yl)ethyl]phenyl}-1,3-thiazol-2-amine;
N-{4-[(1R)-1-(1H-tetrazol-5-yl)ethyl]phenyl}-4-(trifluoromethyl)-1,3-oxazol-2-amine;
4-methyl-N-{4-[(1R)-1-(1H tetrazol-5-yl)ethyl]phenyl}-1, 3-oxazol-2-amine;
5-[(1R)-1-(4-{[4-(trifluoromethyl)-1,3-thiazol-2-yl]amino}phenyl)ethyl]-1H pyrazol-1-ol;
4-methyl-5-[(1R)-1-(4-{[4-(trifluoromethyl)-1,3-thiazol-2-yl]amino}phenyl) ethyl]-1H-pyrazol-1-ol;
5-[(1R)-1-(4-([4-(trifluoromethyl)-1,3-thiazol-2-yl]amino}phenyl)ethyl]-1H-1,2,3-triazol-1-ol;
5-[(1R)-1-(4-{[4-(trifluoromethyl)-1,3-thiazol-2-yl]amino) phenyl)ethyl] isoxazol-3-ol;
4-methyl-5-[(1R)-1-(4-{[4-(trifluoromethyl)-1,3-thiazol-2-yl]amino}phenyl) ethyl]isoxazol-3-ol;
5-[(1R)-1-(4-{[4-(trifluoromethyl)-1,3-thiazol-2-yl]amino}phenyl)ethyl] isothiazol-3-ol;
4-[(1R)-1-(4-{[4-(trifluoromethyl)-1,3-thiazol-2-yl]amino}phenyl)ethyl]-1,2,5-oxadiazol-3-ol;
4-[(1R)-1-(4-{[4-(trifluoromethyl)-1,3-thiazol-2-yl]amino}phenyl)ethyl]-1,2,5-thiadiazol-3-ol;
5-[(1R)-1-(4-{[4-(trifluoromethyl)-1,3-thiazol-2-yl]amino}phenyl)ethyl]-1H 1,2,4-triazol-1-al.

Particularly preferred compounds of formula (II) according to the invention are selected from 1-N-[4-[(1R)-1-(1H-tetrazol-5-yl)ethyl]phenyl}-4-(trifluoromethyl)-11,3-thiazol-2-amine (herein indicated also as DF3966Y) and pharmaceutically acceptable salts thereof, preferably its sodium salt (herein indicated also as DF3966A).

C5aR inhibitors of formula (II) are disclosed in WO2009/050258, that also disclose their method of synthesis, their activity as C5aR inhibitors as well as their use in the treatment of diseases that involve C5a induced human PMNs chemotaxis, such as autoimmune hemolytic anemia (AIHA), psoriasis, bullous pemphigoid, rheumatoid arthritis, ulcerative colitis, acute respiratory distress syndrome, idiopathic fibrosis, glomerulonephritis and in the prevention and treatment of injury caused by ischemia and reperfusion.

The chemotherapy-induced iatrogenic pain according to the invention may be that induced by any chemoterapeutic agent having neurotoxic side effects. Preferably, said chemoterapeutic agent is selected from platinum-based drugs, taxanes, epothilones, plant alkaloids, thalidomide, lenalidomide and pomalidomide, carfilzomib, bortezomib and eribulin. More preferably, said chemoterapeutic agent is selected from cisplatin, carboplatin, oxaliplatin, paclitaxel, cabazitaxel, docetaxel, ixabepilone, vinblastine, vincristine, vinorelbine, etoposide, thalidomide, lenalidomide, pomalidomide, carfilzomib, bortezomib and eribulin. According to a preferred embodiment, the chemotherapy-induced iatrogenic pain is that induced by a taxane, more preferably by paclitaxel.

EXAMPLES

Methods and Materials

Drugs and Reagents

The following materials were obtained from the indicated sources: recombinant mouse C5a was purchased from R&D, lot MJJ0714041, diluted in BSA 0.1% and kept at −70° C. Paclitaxel (Evotaxel® Evolabis, lot A37053) was kept at 4° C., and diluted in saline at the moment of use. For intrathecal injections the vehicle used was aCSF (artificial cerebrospinal fluid), from Tocris.

Biochemical Kits and Reagents

CellTag 700 Stain ICW Kit (Li-cor #cat. 926-41091)
Gro/KC, Peprotech #cat. 400-10

Recombinant Rat CXCL1/GRO alpha/KC/CINC-1 Protein—R&D Systems cat. #515-CN lot 44SO$_{211121}$ Paclitaxel (Taxol)—Tocris—R&D systems #1097 lot 7A/177205

C5a component—recombinant mouse complement—R&D Systems #2150-c5 lot MJJ0715041

Hoechst 33342—Thermo Fischer Sc. #H3570

Animals

The experiments were performed in male Balb/c wild type (WT) and in C5aR deficient (C5aR$^{-/-}$) mice (6-8 weeks age). For the experiments with DF2593A, animals were housed in the animal care facility of the Ribeirao Preto Medical School, University of Sao Paulo, in plastic cages at 20° C.±1° C. with water and food ad libitum and controlled light/dark cycle. When done oral acute treatment, animals were kept without food for 2-4 hours. Animals were taken to the testing room at least 1 h before experiments and were used only once. Animal care and handling procedures were in accordance with the International Association for the Study of Pain guidelines and with the control of Animal Ethic Committee from Ribeirao Preto Medical School, protocol 120/2014.

For the experiments with DF3966A, animals were housed in the animal care facility of the Department of Pharmacy of the University of Naples, Italy, in a room with controlled temperature (22±1° C.), humidity (60±10%) and light (12 h per day); food and water were available ad libitum. All behavioural tests were performed between 9:00 AM and 5:00 PM, and the animals were used only once. Animal care and manipulations were conducted in conformity with International and National law and policies (EU Directive 2010/63/EU for animal experiments, ARRIVE guidelines and the Basel declaration including the 3R concept). The procedure reported here were approved by the Institutional Committee on the Ethics of Animal Experiments (CVS) of the University of Naples Federico II and by Ministero della Salute under protocol n. 2014-00884607.

CIIP (Chemotherapy-Induced Iatrogenic Pain) Experimental Protocol

The protocol used was performed according POLOMANO et al., 2001, adapted to mice. The animals received paclitaxel 4 mg/kg intraperitoneally (i.p.) for four alternate days (days 1, 3, 5, and 7). During treatment period, mechanical and cold allodynia were measured 4 hours after the injection of paclitaxel.

Acute Post Treatment

DF2593A was orally given in dose of 1 mg/kg at 8 and 14$^{th}$ days after first paclitaxel injection. The effect of drug was evaluated 2, 4, 6 and 24 hours after administration.

Chronic Pre Treatment

DF2593A was given orally in a dose of 1 mg/kg, 12 in 12 hours, for 7 days during the induction phase of CIIP. On days 1, 3 5 and 7, the administration of DF2593A was 1 hour before paclitaxel.

DF3966A was administrated 30 mg/kg/os from 1$^{st}$ at 14$^{th}$ day (twice daily; 8.00 am and 20.00 pm). On day 1-3-5-7 DF3966A was administrated 1h after paclitaxel.

Intrathecal Treatment

DF2593A in doses of 10, 30 or 100 µg/5 µL was injected at 8 and 14$^{th}$ days after the first injection of paclitaxel (CIIP).

Recombinant mouse C5a was given by intrathecal way, in a volume of 5 µL, and its effect follows for 1, 3, 5, 7 and 24 hours after injection.

Mechanical Nociceptive Paw Test

In DF2593A experiments, mechanical hyperalgesia was tested using von Frey filaments. Mice were placed in acrylic cages (12×10×17 cm) with wire grid floors in a quiet room 15-30 minutes before the start of testing. A crescent series of filaments were applied on right paw of CIIP mice. The lower filament able to elicit flinching movements was recorded as the mechanical threshold. The animals were tested before and after treatments and the results are expressed as log of mechanical threshold.

In DF3966A experiments, sensitivity to tactile stimulation was measured using the Dynamic Plantar Aesthesiometer (DPA, Ugo Basile, Italy). Animals were placed in a chamber with a mesh metal floor covered by a plastic dome that enabled the animal to walk freely, but not to jump. The mechanical stimuli were then delivered in the mid-plantar skin of the hind paw. The cut-off was fixed at 50 g. Testing was performed on both paws before paclitaxel first administration and then on 3$^{rd}$, 5$^{th}$, 7$^{th}$, 10$^{th}$ and 14$^{th}$ days after paclitaxel first administration.

Cold Allodynia—Acetone Test

In the same apparatus of von Frey test, and nearly 15 minutes after the mechanical test, was performed the acetone test. With a 1 mL syringe, one drop (50 µL) of pure acetone was released allowing the spreading of liquid for the both paw surfaces (dorsal and plantar). All movements as licking, flinching or lifting of paw were recorded with a chronometer in a total testing time of 2 minutes.

Heat Latency—Hargreaves Test

Hargreaves test was performed as previous described (HARGREAVES et al., 1988). The animals were habituated on a glass surface with controlled temperature, which allow the homogeneous delivery of infrared light on the paw. After the activation of the light source, a chronometer was turned on. A crescent temperature reached the paw and the chronometer was turned off as soon as the animal did a withdraw movement out the light. The time recorded was considered the heat latency. A cut off of 20 seconds was fixed to avoid damage to paw. The results are expressed in seconds.

Primary Cultures of Dorsal Root Ganglion (DRG) Neurons

Dorsal Root Ganglion neurons were obtained by dissociation of post natal (P2) Sprague Dawley rat ganglia (Envigo, Bresso Italy), following well-defined protocols (O'Meara et al, 2011; Owen et al, 2012). To minimize introduction of contaminating cells into the culture, any excessively long roots were trimmed from DRGs. After the isolation, DRGs were enzymatically dissociated as follows:

20 minutes of 1.5 mg/ml papain exposure at 37° C., 30 minutes of 4 mg/ml collagenase exposure at 37° C.

Subsequently, cells were mechanically dissociated with a fire polished glass Pasteur pipette, in order to obtain a single cell suspension.

Once dissociation was achieved, cells were seeded onto 96 black multiwell plates coated with Laminin (10 ug/mL, overnight at Room Temperature, RT) at selected densities. Following 1 week of incubation in DMEM high glucose medium supplemented with 10% FBS, 1× N2, 1× B27, 100 IU/ml penicillin, 10 mg/ml streptomycin, cells were treated according to experimental needs.

In—Cell Western Analysis for α-Tubulin Evaluation

Dorsal Root Ganglion neurons isolated as previously reported were subjected to the following experimental challenge scheme as depicted in FIG. 10.

Paclitaxel, C5a and drugs were administered 24 hr prior the in-cell western experiment. Following 24 hr of treatment with appropriate stimuli as previously indicated, cells were washed with 1×PBS and fixed with 3,7% formaldehyde for 15 min. After the removal of fixing solution, cells were washed with 1×PBS and permeabilized with 1×PBS-0,1% Triton X-100 for 5 min at RT. Cells were then stained over night at 4° C. with the anti-acetylated α-Tubulin antibody, diluted 1:500 in Odyssey Blocking buffer, following manufacturer's protocol.

The next day, cells were washed with 1×PBS-0.1% Tween20, and stained with the secondary antibody (diluted 1:800 in Odyssey Blocking buffer, as recommended by the protocol) and with the CellTag 700Stain 0,2 M. To lower the background, Tween20 at a final concentration of 0.2% was added to the Odyssey Blocking buffer. 96-well plates were then read at Odyssey CLx Imaging system and images acquired. Data analysis was carried out by the use of Image Studio 2.1 software.

Alpha Tubulin Acetylation DRG-derived neurons were cultured for 7 days and then treated with:

paclitaxel (200 nM, 500 nM, 1 μM and 5 μM, 20 μM) in presence or absence of DF3966Y (0.1, 1 and 10 μM) or DF2593A (0.1, 1 and 10 μM)

or C5a (500 ng/ml and 1 μg/ml) in presence or absence of DF3966Y (1 μM)

After 24 hr of treatment, cells were stained by immunofluorescence.

Immunofluorescence

Cells were fixed with saccharose-paraformaldehyde then staining was performed overnight. Primary antibodies (anti—Ill Tubulin and anti-synaptotagmin 1) were diluted 1:500 in 1×PBS-4% BSA-2% Normal goat serum and 0.3% Triton x-100. The next day, cells were washed with 1×PBS-4% BSA and secondary antibodies were used diluted 1:500 in 1×PBS-4% BSA-2% Normal goat serum and 0.3% Triton x-100. After 1 hr of incubation, cells were washed with 1×PBS. Hoechst was used as a counterstain.

Image Analysis

Sixteen images per well were taken with ArrayScan XTI HCA Reader (Thermo Fisher Scientific) with and 40× objective. All the analysis were done with HCS Studio software (Thermo Fisher Scientific).

For synapse count a threshold has been set, in particular all the objects, positive to synaptotagmin staining, in the range 0.365-2.457 μm$^2$ have been considered as synapses.

Electrophysiological Treatment

Dorsal Root Gangliar (DRG)-derived neurons were cultured for 7 days and then treated in blind with the following combinations: 10 nM Paclitaxel, 10 nM Paclitaxel+1 μM DF3966Y, 1 μg/ml C5a, 1 μg/ml C5a+1 μM DF3966Y.

The compounds were administered for 1 min 30 sec (short acute stimulation) or 5 minutes (long chronic stimulation). The application of the compounds was followed by a wash-out in the physiological control solution for an equivalent time (about 10 min).

Electrophysiological Recordings

Electrophysiological recordings were performed by the patch-clamp technique in the whole-cell configuration. The standard extracellr solution was bath applied and contained the following (mM): NaCl 135, KCl 2, CaCl2 2, MgCl2 2, hepes 10, glucose 5, pH 7.4. The standard pipet solution contained the following (mM): potassium aspartate 130, NaCl 10, MgCl2 2, CaCl2 1.3, EGTA 10, Hepes 10, pH 7.3. Recordings were acquired by the pClamp8.2 software and the MultiClamp 700A amplifier (Axon Instruments), in current-clamp mode.

Data Analysis

For the in vivo experiments, data are reported as the means±SEM. The letter N in the legends refers to the number of mice used in each experimental group of each experiment. The differences between the experimental groups were compared by ANOVA (one-way), and individual comparisons were subsequently made with Bonferroni post hoc test. Two-way ANOVA was used to compare the groups when the hypernociceptive responses were measured at different times after the stimulus injection. $P<0.05$ were considered significant.

Results

Figure 1:
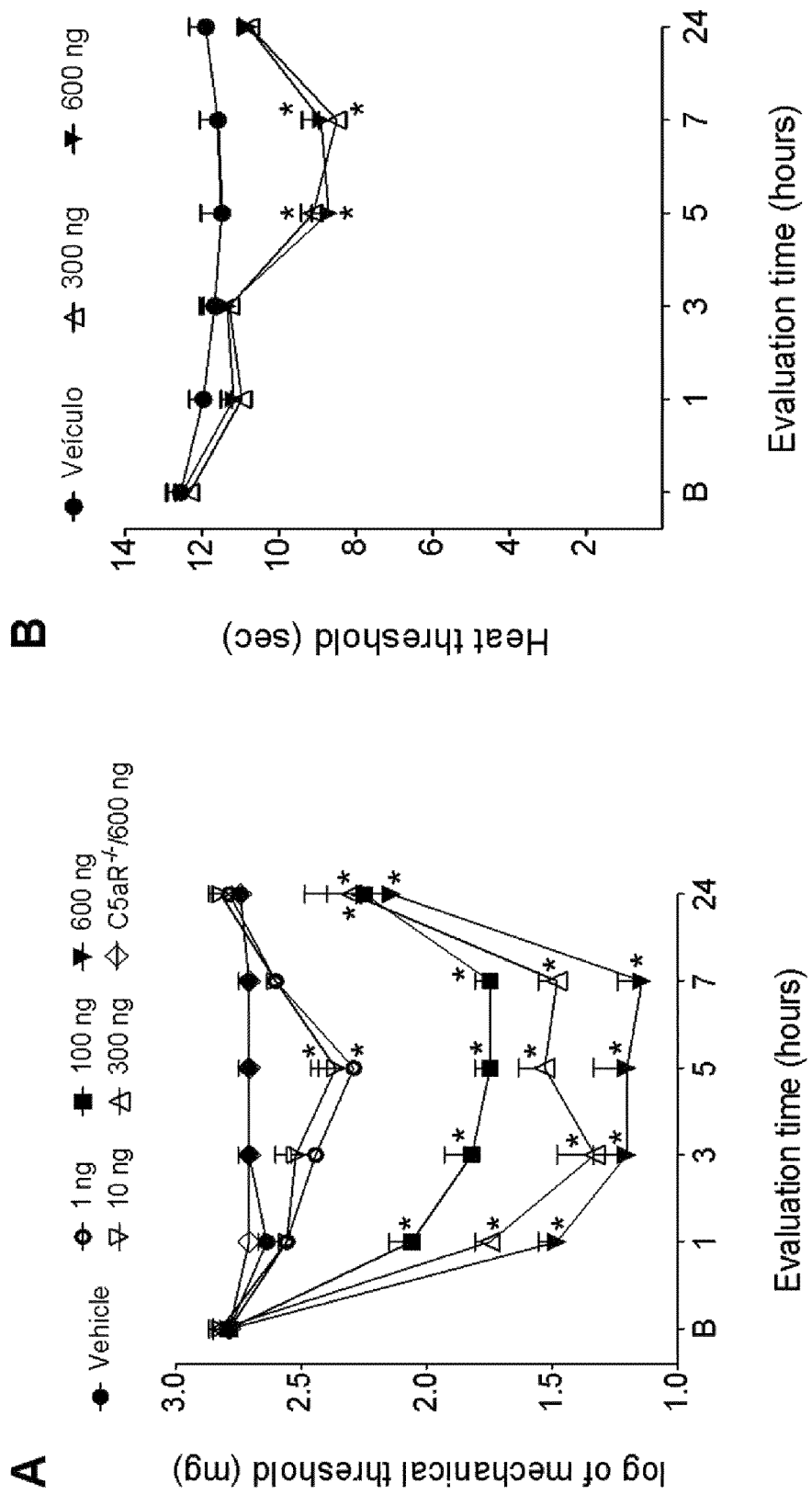
FIG. 1. Dose-response curve of intrathecal injection of recombinant C5a (1, 10, 100, 300 and 600 ng/5 µL) in male Balb/C mice. A, mechanical threshold—von Frey hair test- and B, thermal threshold—Hargreaves—test. B, baseline. Data represented by mean±SEM. N=5. Statistical analysis was performed by two-way ANOVA, post-hoc Bonferroni's test. *P<0.05 compared to vehicle.

Intrathecal Injection of Recombinant C5a Reduce Mechanical and Thermal Nociceptive Threshold The present results showed that intrathecal injection of recombinant C5a (100, 300 and 600 ng/5 μL) in mice promoted reduction of mechanical threshold in a dose-dependent manner, up to 24 hours after injection. C5a pro-nociceptive effect was abrogated in C5aR$^{-/-}$ mice. The higher doses also caused a decrease in heat latency between 5 and 7 hours after injection (FIGS. 1, A and B).

The Absence of C5a/C5aR Determines Less Development of Iatrogenic Pain

Figure 2:
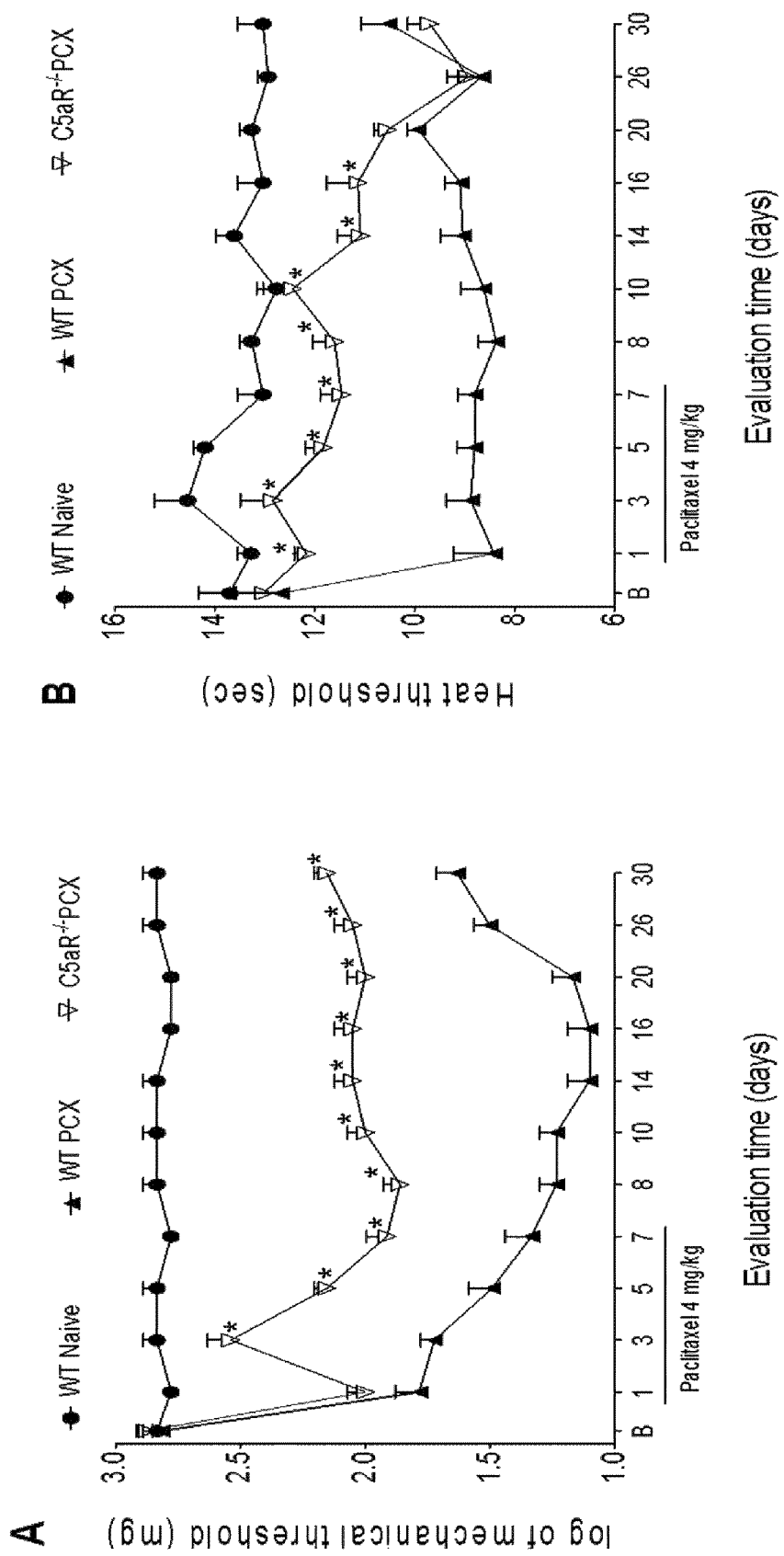
FIG. 2. A, mechanical threshold—von Frey hair test—and B, thermal threshold—Hargreaves test—during chemotherapy-induced iatrogenic pain (CIIP) development in male Balb/C mice. B, baseline; PCX, paclitaxel; WT, wild type. Data represented by mean±SEM. N=5. Statistical analysis was performed by two-way ANOVA, post-hoc Bonferroni's test. *P<0.05 compared to WT PCX group.

The present inventors demonstrated that both genesis and maintenance of CIIP are compromised in C5aR$^{-/-}$ animals. In fact, there is less mechanical (FIG. 2, A) and heat (FIG. 2, B) hypersensitivity development in C5aR$^{-/-}$ mice during both, induction and maintenance phases of CIIP.

These results pointed out the relevance of C5a in CIIP, showing its role in sensitization of different pain pathways and fibres, and embracing important clinical symptoms.

Example 1

Effect of DF2593A in CIIP

Figure 3A:
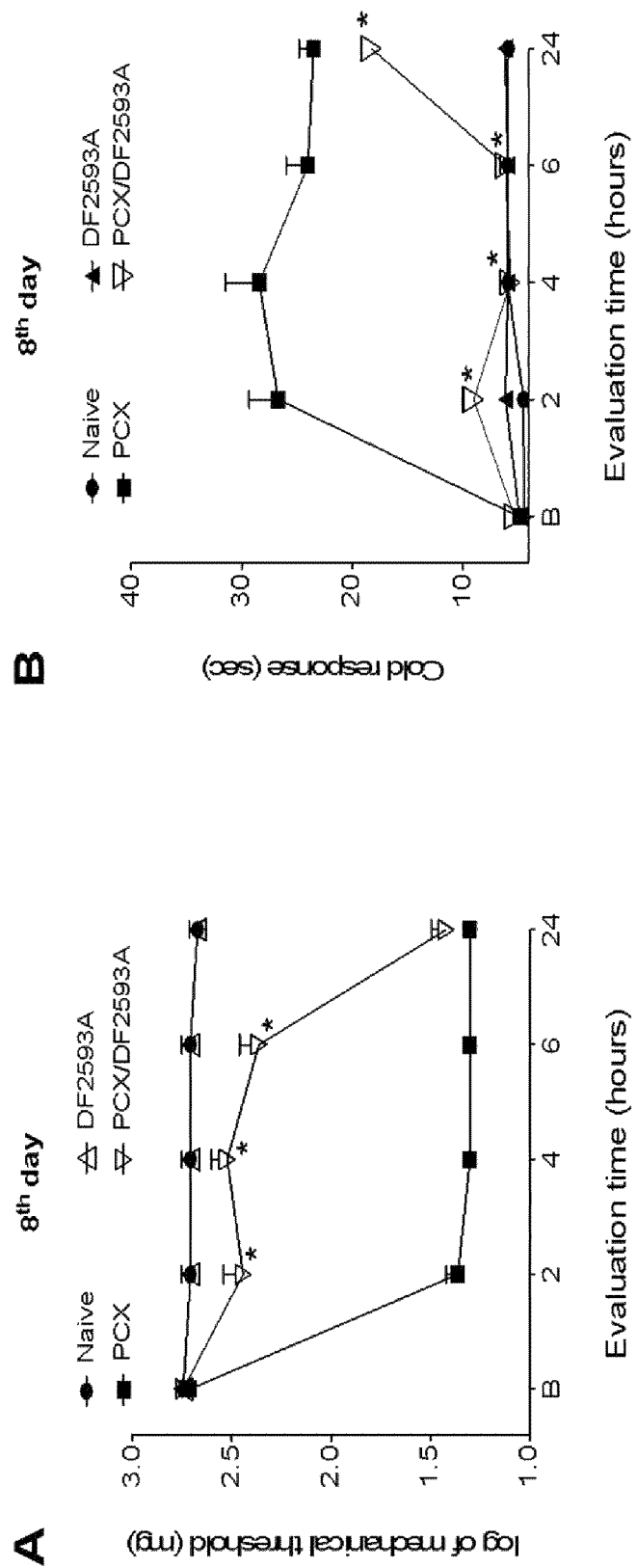
FIGS. 3a, 3b. Mechanical threshold (A and C) and cold response (B and D) in male Balb/C mice, after oral treatment with 1 mg/kg of DF2593A (arrow) at 8 (A and B) or 14 (C and D) days after first injection of PCX, paclitaxel. B, baseline. Data represented by mean±SEM. N=5. Statistical analysis was performed by two-way ANOVA, post-hoc Bonferroni's test. *P<0.05 compared to PCX group.
Figure 3B:
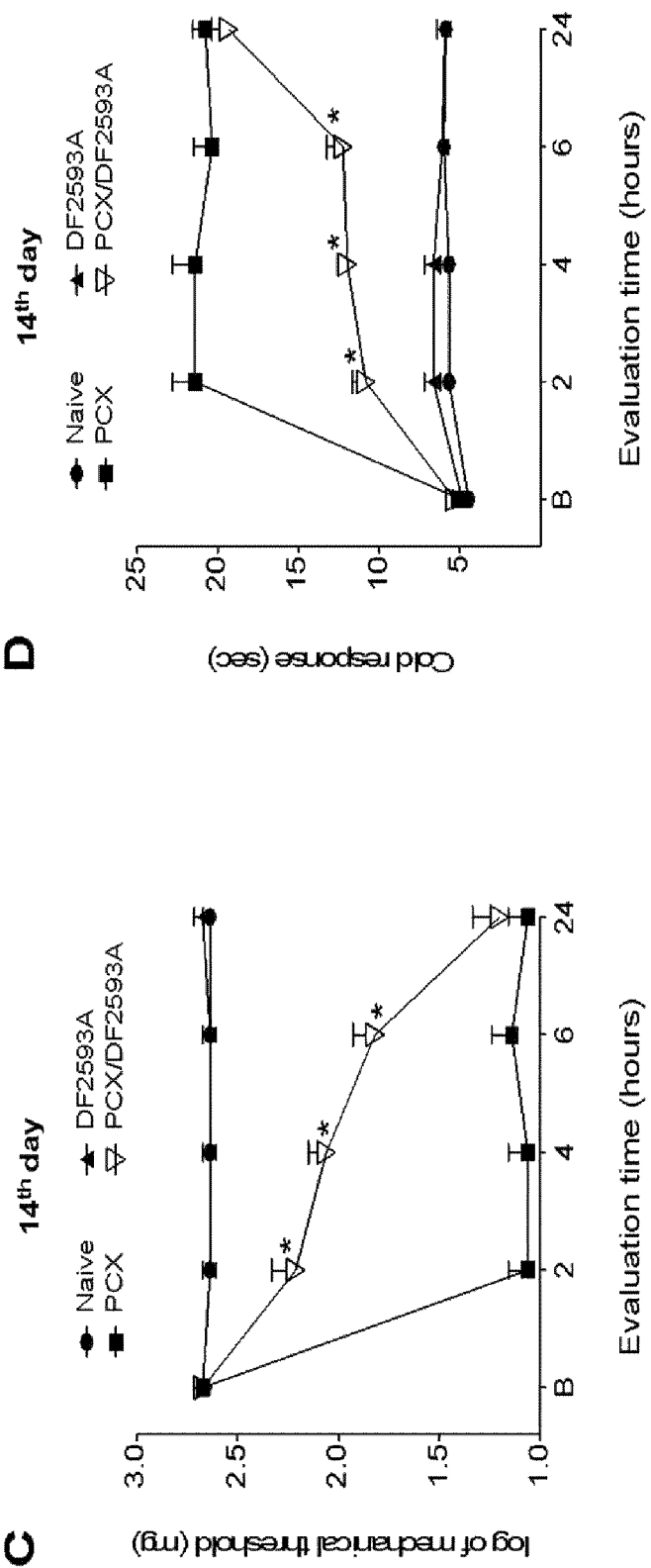

Oral administration of 1 mg/kg of DF2593A in male mice is able to reduce the mechanical hypersensitivity during both phases of CIIP: end of induction, at 8$^{th}$ day (FIG. 3a, A) and established, at 14$^{th}$ day (FIG. 3b, C). Besides that, the cold response (FIG. 3a, B and FIG. 3b, D) resulted from CIIP is reduce after DF2593A treatment. Those effects are observed since 2 until 6 hours after drug administration. Taken together, those data show that oral therapeutic treatment with DF2593A in an established pain condition is able to reduce mechanical and cold hypersensitivity resulted from physical or chemical nerve lesion, for at least 6 hours after administration.

Example 2

Figure 4:
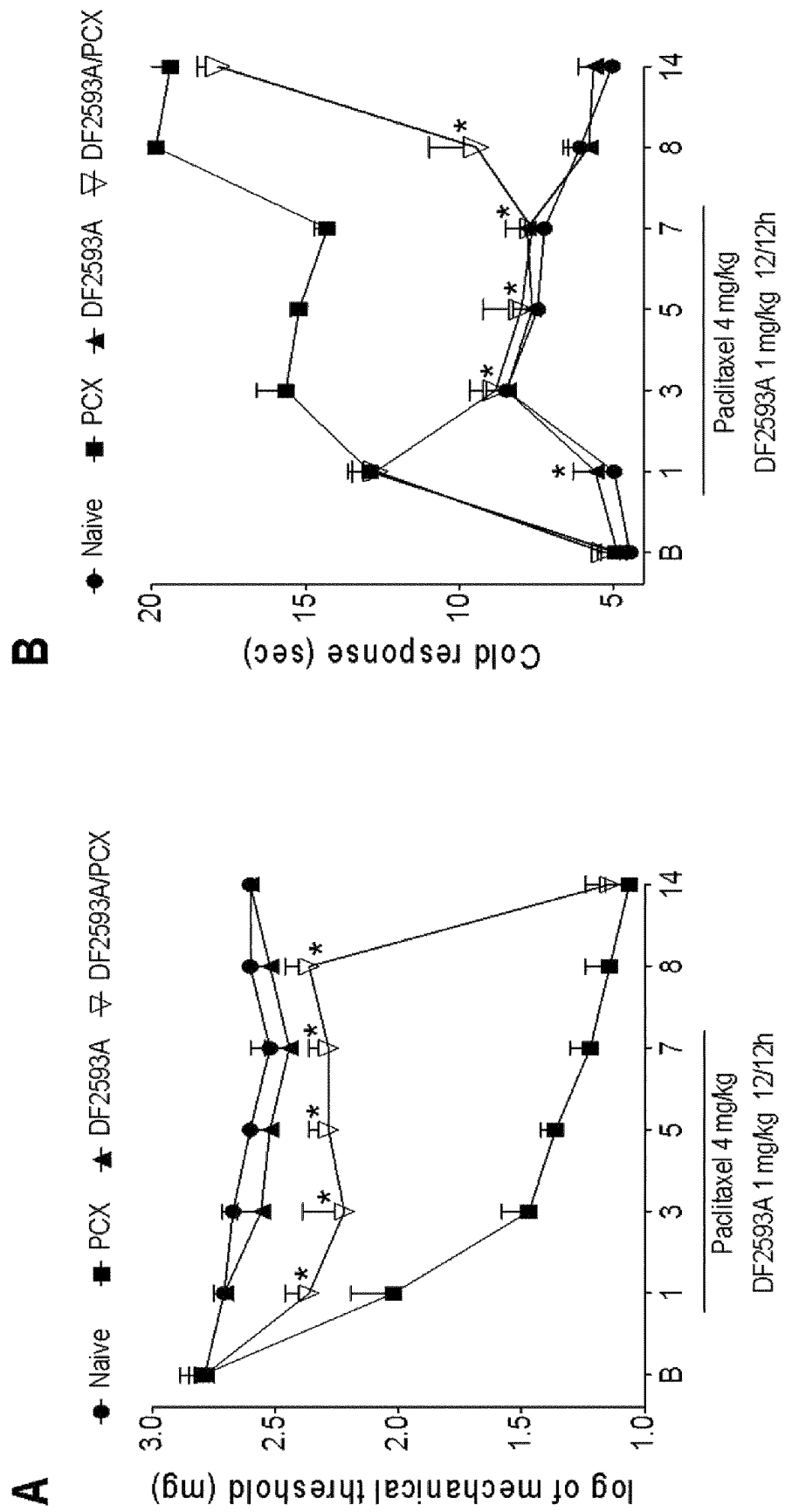
FIG. 4. A, mechanical threshold—von Frey hair test and B, cold response—acetone test, during chemotherapy-induced iatrogenic pain (CIIP) development in Balb/C male mice. B, baseline. Animals were treated with DF2593A 1 mg/kg, orally, 12 in 12 hours, for 7 days. On days 1, 3 5 and 7, the administration of DF2593A was 1 hour before paclitaxel (PCX). The measures were done 4 hours after PCX injection. Data represented by mean±SEM. N=5. Statistical analysis was performed by two-way ANOVA, post-hoc Bonferroni's test. *P<0.05 compared to PCX group.

Systemic Treatment with DF2593A, During Induction of CIIP, Prevents Development of Iatrogenic Pain When given chronically, during the induction phase of CIIP, DF2593A prevents the development of mechanical (FIG. 4, A) and cold (FIG. 4, B) nociceptive responses, although only during the treatment. Two daily doses (12/12 hours) of DF2593A 1 mg/kg p.o. were given to mice with no food restriction, since the first day until 7$^{th}$ day of CIIP model. The drug was given always 1 hour before the administration of paclitaxel. Animals were measured at baseline and then every day from the first paclitaxel injection until 8$^{th}$ day, a time point with established pain.

The drug is able to efficiently prevent the development of mechanical and cold response during the induction phase of CIIP. However, no effect is observed 24 hours after the last DF2593A dose, corroborating with previous results and with the pharmacokinetic profile of the drug.

Figure 5A:
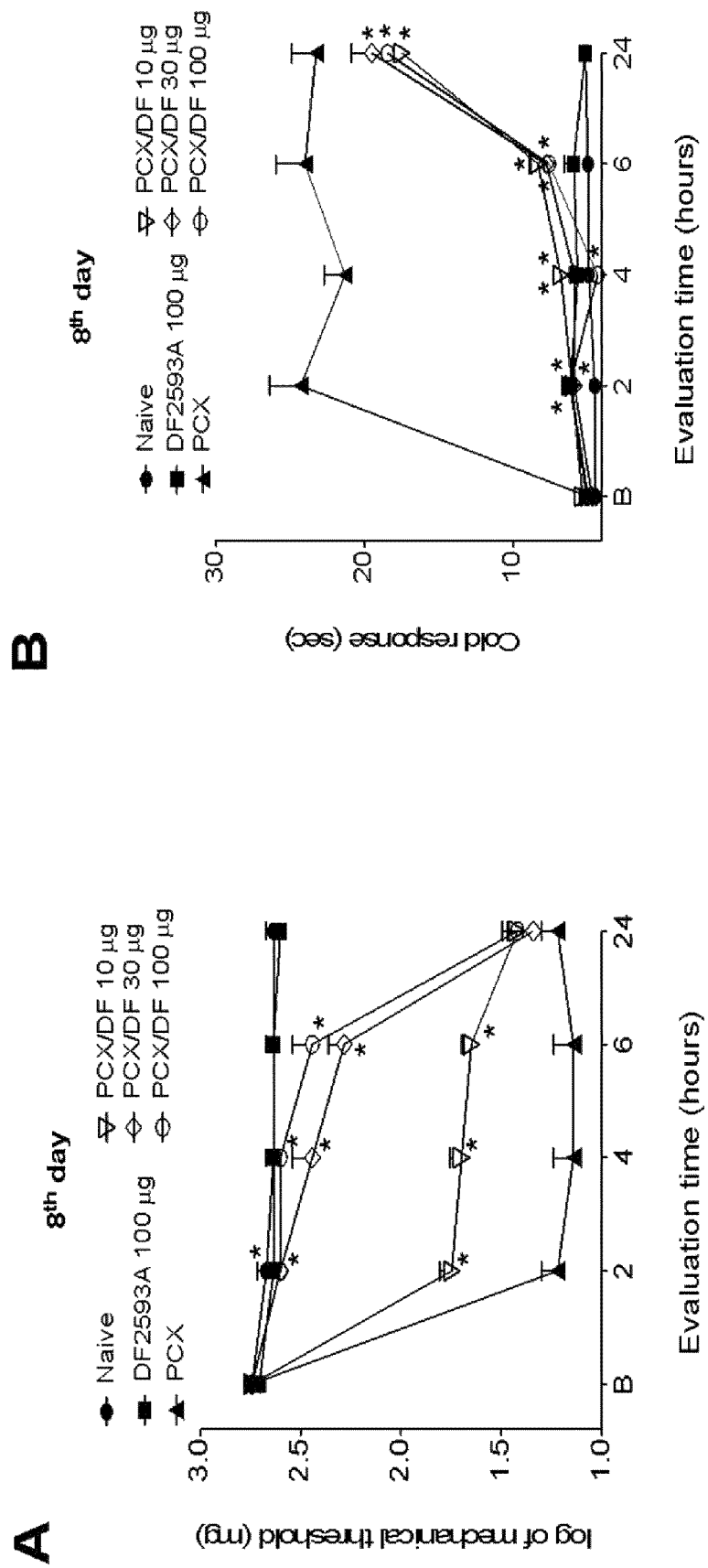
FIGS. 5a, 5b. Mechanical threshold (A and C) or cold response (B and D) in male Balb/C mice after intrathecal treatment with different doses of DF2593A, 8 (A and B) and 14 (C and D) days after the first injection of paclitaxel (PCX). B, baseline. Data represented by mean±SEM. N=5. Statistical analysis was performed by two-way ANOVA, post-hoc Bonferroni's test. *P<0.05 compared to PCX group.
Figure 5B:
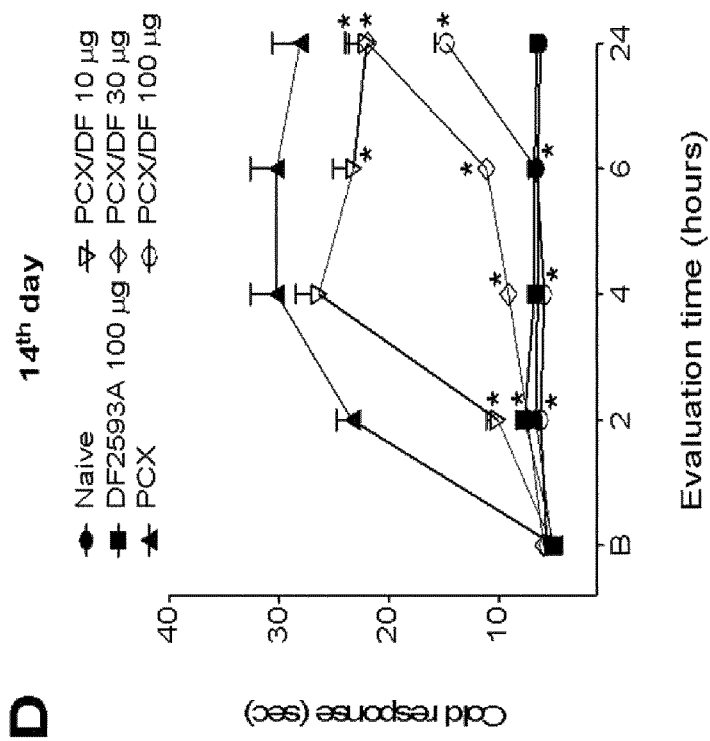
Figure 5B:
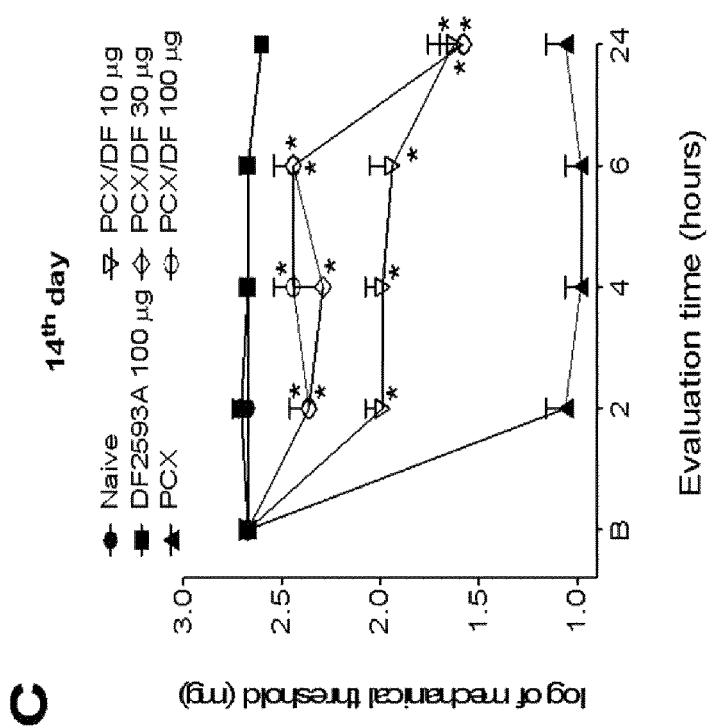

Likewise, the injection of 10, 30 or 100 μg/5 μL of DF2593A by intrathecal route, in male mice with established CIIP (8 and 14$^{th}$ day), is able to reduce the nociceptive behaviour and improves mechanical and cold allodynia. The most relevant effect is observed with the higher doses: 30 and 100 µg/5 µL at 8$^{th}$ day (FIG. 5a, A and B), although the efficacy of 10 µg/5 µL is still statistically significant.

Example 3

Effect of DF3966A in Paclitaxel-Induced Mechanical and Cold Allodynia

Following paclitaxel administration, vehicle control group (CTR) showed an evident mechanical and cold allodynia as compared to Sham rats. In particular, in the DPA test, paw withdrawal threshold, resulted significantly reduced at day 5, 7, 10 and 14, evidence of pain (FIG. 6, A).

Figure 6:
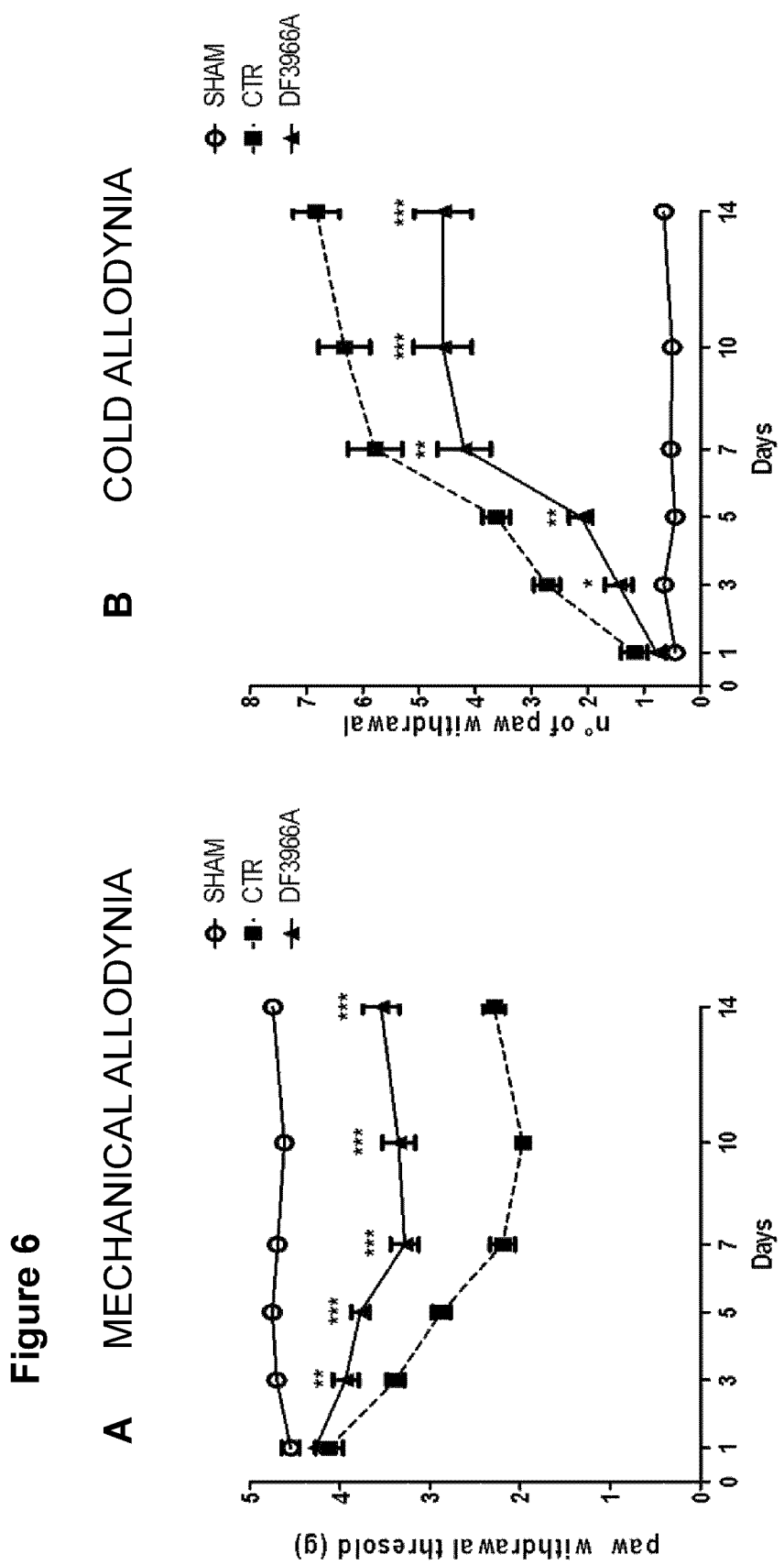
FIG. 6. Mechanical (A) and cold (B) allodynia in male Balb/C mice were evaluated 3h after DF3966A treatment (4h after paclitaxel). The significance of differences between groups were determined by two-way analyses of variance (ANOVA) followed by Bonferroni post hoc tests for multiple comparisons. The level of significance was set at *p<0.05 vs CTR.

Animals treated with DF3966A showed a significant reduction of mechanical allodynia at days 3, 5, 7, 10 and 14 when compared to vehicle control animals (FIG. 6, A). In cold allodynia experiments, in the control group, the numbers of paw withdrawal threshold resulted significantly increased at days 3, 5, 7, 10 and 14, evidence of pain (FIG. 6, B). Animals treated with DF3966A showed a significant reduction of cold allodynia at days 3, 5, 7, 10 and 14 when compared to vehicle control animals. The obtained results clearly show that DF3966A leads to a significant reduction of mechanical and cold allodynia at 5, 7, 10 and 14 days after paclitaxel administration.

Example 4

Effect of DF2593A and DF3966Y on α-Tubulin Levels Under Paclitaxel Treatment

Paclitaxel was given to the DRG neurons following 7 days of culture at the concentration of 200 nM (Scuteri et al. 2006).

As reported in Table 1, 200 nM Paclitaxel showed a marginal yet significant increase in acetylated α-Tubulin, with respect to control (UT) cells.

Example 5

Effect of DF3966Y in C5α-induced neuronal toxicity In order to determine whether the observed effects may be triggered also by C5a, recombinant mouse C5a 1 µg/ml (111.11 nM) was given to the DRG neurons after 7 days of culture in presence or absence of DF3966Y 1 µM.

After 24 hr of incubation, acetylated α-Tubulin was quantified using in-cell western technique, as previously described.

Figure 7:
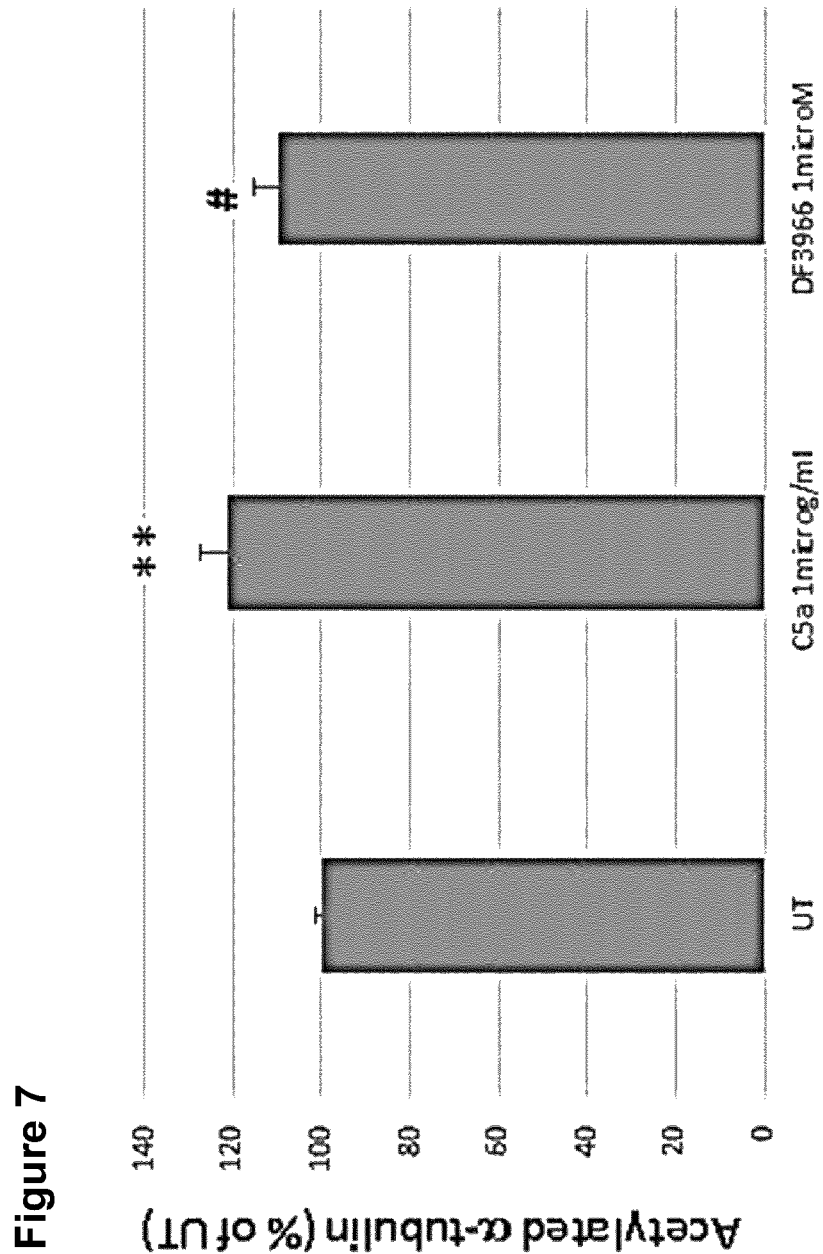

FIG. 7 shows that C5a 1 µg/ml was able to increase the levels of acetylated α-Tubulin and DF3966Y significantly reduced the challenge induced by C5a exposure.

Example 6

Effect of DF3966Y on Neuronal Functionality

Cells number, synapse number and dentritic arborization were evaluated in untreated cells and in cells stimulated with paclitaxel and C5a alone or in presence of the drug. As marker of chemotherapy-induced toxicity, the total number of synapses on DRG neurons was quantitative evaluated as percentage of the number of synapse with respect to untreated (UT) control.

Dendritic arborization directly influences synaptic genesis and input. A well-developed arborization indicates a functional synaptic network. For this reason, the area occupied by dendritic arborization has been quantified.

Data are obtained as the sum of the values obtained by the analysis of sixteen fields per well for each experiment. Percentage of the values in respect to the relative mean untreated group was calculated. Mean of the percentages from 4 separate experiments was plotted in the following Tables 2-7.

TABLE 1

| | Acetylated α-Tubulin (% of UT) | | | | | | |
|---|---|---|---|---|---|---|---|
| | UT (control) | Paclitaxel (200 nM) | DF2593A (0.1 µM) | DF2593A (1 µM) | DF2593A (10 µM) | DF3966Y (0.1 µM) | DF3966Y (1 µM) | DF3966Y (10 µM) |
| Mean ± SD | 100.12 ± 2.21 | 111.41 ± 5.43* | 107.38 ± 18.61 | 100.67 ± 11.29 | 70.72 ± 10.11*## | 76.45± 7.61*## | 65.16 ± 12.65*## | 89.05± 6.11## |

Data are mean ± SD of 2 different experiments.
*p < 0.05 vs UT;
p < 0.05 vs Paclitaxel;
p < 0.01 vs Paclitaxel As shown in Table 1, the compound DF2593A seems to revert the Paclitaxel effect in a dose-dependent manner. In particular, when applied at 0.1 µM concentration, the drug is not able to revert the Paclitaxel-induced increase in acetylated α-Tubulin. When DF2593A was applied at 1 µM concentration, the drug reverted the Paclitaxel-induced challenge and the observed levels of acetylated α-Tubulin were similar to control (UT) cells. At 10 µM, the drug seems to exert a significant beneficial effect on DRG neurons with a reduction in acetylated α-Tubulin of about 25% with respect to control (UT) cells. The compound DF3966Y (0.1, 1, 10 µM) significantly reverted the Paclitaxel-induced challenge. At the lowest concentrations tested (0.1 µM and 1 µM), the drug seems to exert a beneficial effect on DRG neurons.

TABLE 2

Cells number under PAC (Paclitaxel) and DF3966Y alone or in combination. Data are mean ± SD of 3 different experiments.

| | % of cell number | | | |
|---|---|---|---|---|
| | UT (control) | Paclitaxel | DF3966Y (1 µM) | DF3966Y (1 µM) + PAC |
| Mean ± SD | 100 | 88.87 ± 6.04 | 101.55 ± 10.59 | 98.83 ± 12.49 |

The administration of Paclitaxel to DRG neurons induced a slight decrease in cell number. This effect may be due to the presence of proliferating cells (Purkinje cells) on which paclitaxel exerted its anti-proliferative effect and not to a real neuronal death. Accordingly, the treatment with DF3966Y, either when administered alone or when administered with PAC, did not exert any significant effect on cell number.

TABLE 3

Cells viability under C5a and DF3966Y alone or in combination.
Data are mean ± SD of 2 different experiments.

| | % of cell number | | | |
|---|---|---|---|---|
| | UT (control) | C5a | DF3966Y (1 μM) | DF3966Y (1 μM) + C5a |
| Mean ± SD | 100 | 98.69 ± 4.22 | 96.96 ± 6.45 | 96.65 ± 10.77 |

The obtained results indicate that C5a did not induce neuronal death, either when administered alone or in combination with DF3966Y 1 μM.

TABLE 4

Synapse number under PAC and DF3966Y alone or in combinations.
Data are mean ± SD of 3 different experiments.

| | % of synapse number | | | |
|---|---|---|---|---|
| | UT (control) | PAC | DF3966Y (1 μM) | DF3966Y (1 μM) + PAC |
| Mean ± SD | 100 | 88.02 ± 2.99 | 99.89 ± 12.94 | 92.04 ± 21.01 |

Paclitaxel induced a marked decrease in synapse number. The treatment with DF3966Y 1 μM significantly counteracted Paclitaxel-induced effect.

These data clearly indicate a positive effect of 1 μM DF3966Y on neuronal function impairment induced by chemotherapy.

TABLE 5

Synapse number under C5a and DF3966Y alone or in combination.
Data are mean ± SD of 3 different experiments.

| | % of synapse number | | | |
|---|---|---|---|---|
| | UT (control) | C5a | DF3966Y (1 μM) | DF3966Y (1 μM) + C5a |
| Mean ± SD | 100 | 116.90 ± 17.43 | 99.89 ± 12.94 | 111.33 ± 9.27 |

Data show that C5a did not induce neuronal activity damage under these experimental conditions.

TABLE 6

Dendritic tree area under paclitaxel and DF3966Y alone or in combination. Data are mean ± SD of 3 different experiments.

| | % dendritic tree area | | | |
|---|---|---|---|---|
| | UT (control) | PAC | DF3966Y (1 μM) | DF3966Y (1 μM) + PAC |
| Mean ± SD | 100 | 92.22 ± 3.47 | 103.07 ± 8.17 | 101.21 ± 7.97 |

A non-significant decrease in the area occupied by dendritic arborization was induced by paclitaxel and the treatment performed with DF3966Y seems to counteract such a decrease.

These findings are in line with the results obtained by quantification of synapse number, indicating a toxic effect of paclitaxel on neuronal function and a positive effect of the compound.

TABLE 7

Dendritic tree area under C5a and DF3966Y alone and in combination.
Data are mean ± SD of 3 different experiments.

| | % dendritic tree area | | | |
|---|---|---|---|---|
| | UT (control) | C5a | DF3966Y (1 μM) | DF3966Y (1 μM) + C5a |
| Mean ± SD | 100 | 102.68 ± 9.48 | 103.07 ± 8.17 | 106.45 ± 9.43 |

Data shows that acute stimulation is not sufficient to induce cellular damage. The described results clearly indicate a detrimental effect of paclitaxel on neuronal functionality. On the other side, C5a did not show any significant effect on neuronal function at this time point, likely because it could be a late mediator of chemotherapy-induced neuronal toxicity.

The treatment with DF3966Y exerted a beneficial effect, counteracting the paclitaxel-induced loss of neuronal synapses.

Example 7

Figure 8:
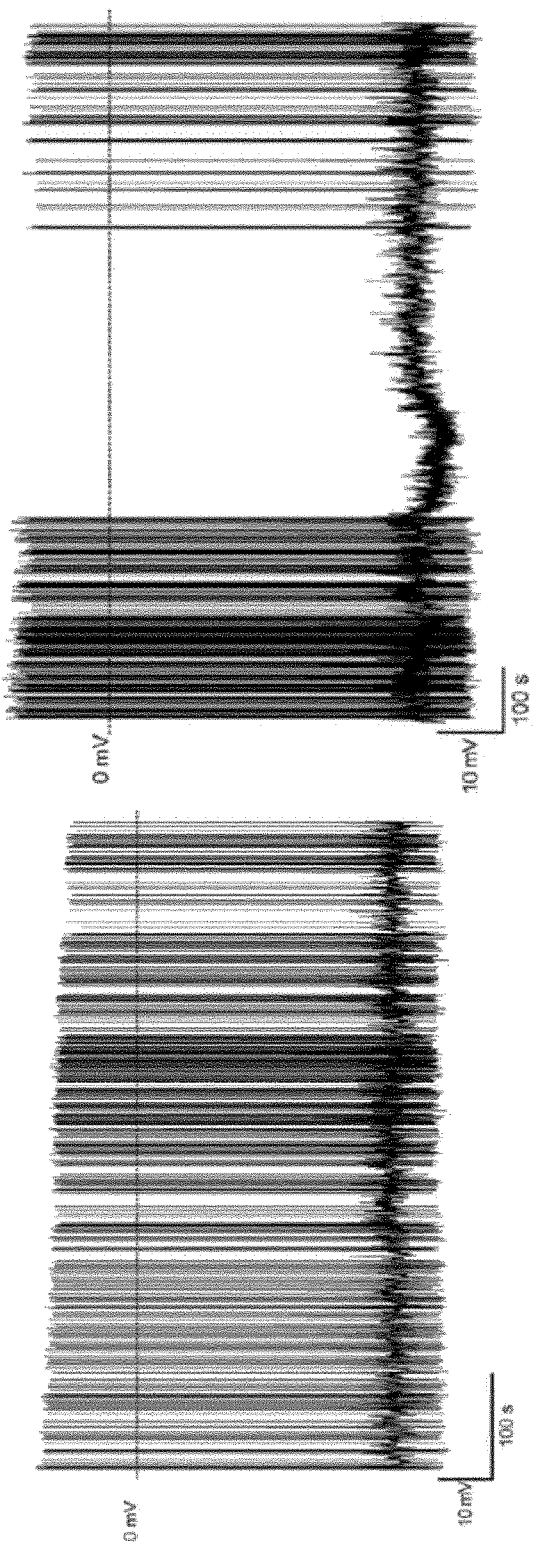
FIG. 8. Representative trace of electrophysiological recordings in DRG cells maintained under basal conditions; Treatment A) Representative trace of electrophysiological recordings in DRG cells challenged with Paclitaxel; Treatment B) Representative trace of electrophysiological recordings in DRG cells challenged with Paclitaxel+DF3966Y.
Figure 8:
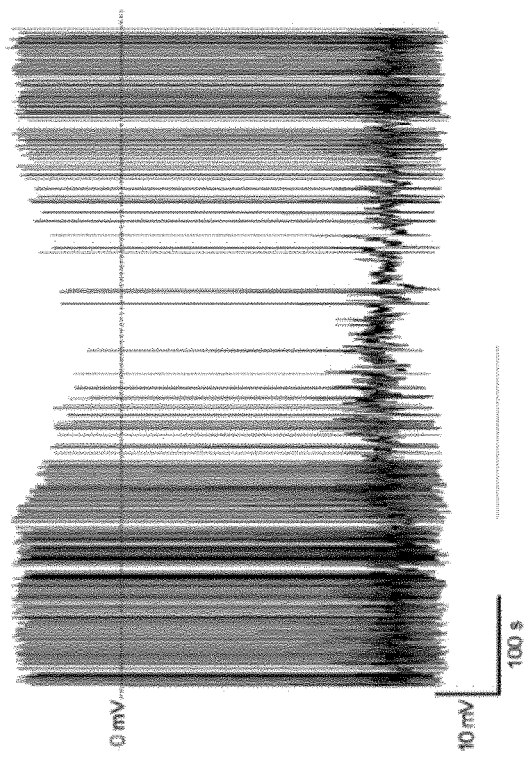

Effect of DF3966Y and Paclitaxel on electrophysiology of DRG The action potential firing rate of DRG neurons in the physiological control solution remained stable for long time, up to 30-40 minutes, as shown in the FIG. 8 (basal condition).

When Paclitaxel was administered (FIG. 8—treatment A), there was an immediate and significant increase of the action potential firing rate (+54.64% vs CTRL), typical of a depolarization phase, which was then followed by a drop in the electrical activity at longer times of exposure (−83.51% vs CTRL), due to inactivation of the voltage gated channels. The effect recovered completely with the administration of the control physiological solution.

When Paclitaxel was administered in the presence of DF3966Y (FIG. 8—treatment B), no significant alteration of electrical activity was observed either in the first immediate phase or at longer time of exposure. Thus DF3966Y seems to be able to completely restore the electrical activity altered by Paclitaxel exposure, both at short as well as at longer timings of exposure.

Example 8

Figure 9:
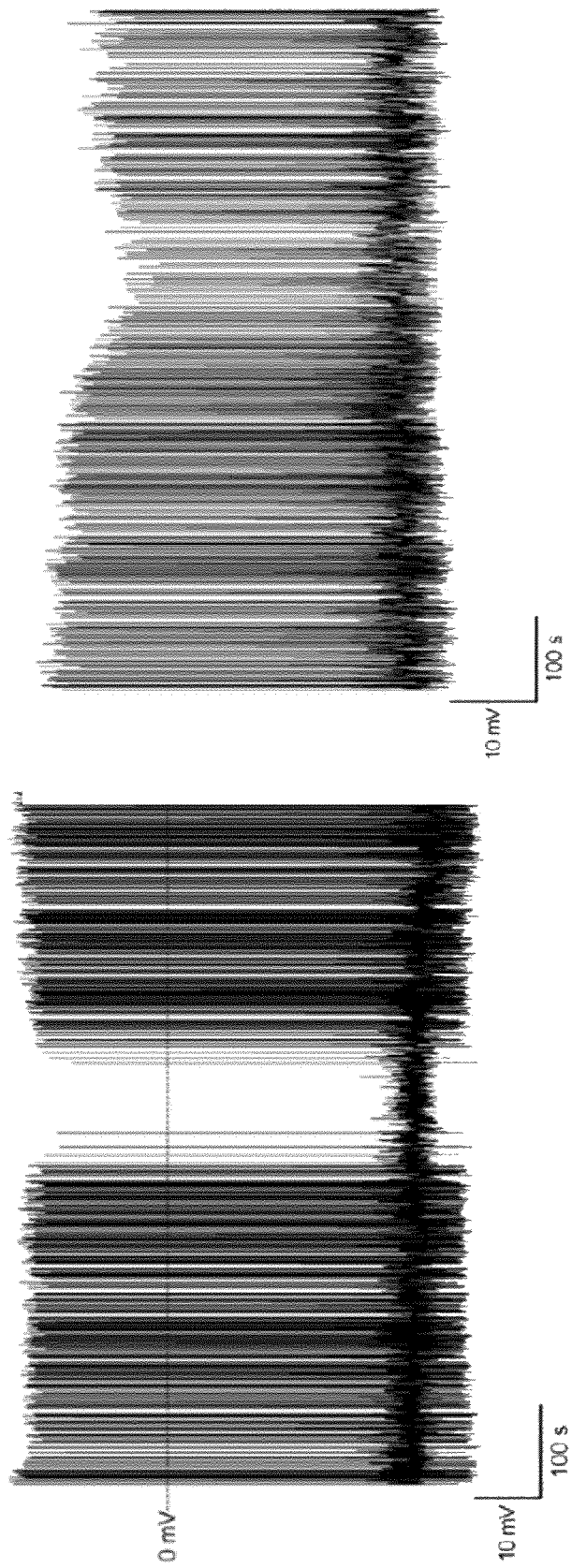

Effect of DF3966Y and C5a on electrophysiology of DRG When C5a was administered to DRG neurons (FIG. 9—treatment C), it was observed an immediate increase of the firing rate (+55.61%) which was followed by a significant reduction of electrical activity (about 70% reduction) at longer times of exposure. The effect recovered completely with the administration of the control physiological solution.

When C5a was administered to DRG neurons in the presence of DF3966Y (FIG. 9—treatment D), no significant alteration of the electrical activity at short time points was observed. Moreover, at longer time of exposure (3-5 minutes), DF3966Y inhibited by about 35% the electrical activity, thus ameliorating C5α-induced effect. The effect recovered completely with the administration of the control physiological solution. Both challenges (Paclitaxel and C5a), when administered alone, exert a detrimental action on DRG neurons, although with different entity: Paclitaxel is more potent stimulus than C5a.

The immediate effect observed upon acute stimulation is (in the case of Paclitaxel and C5a) an increase in the firing rate, typical of a depolarization phase, which is then followed by a drop in the electrical activity at longer times of exposure, due to inactivation of the voltage gated channels.

This effect is counteracted by DF3966Y, in particular upon Paclitaxel stimulation.

The invention claimed is:

1. A method of preventing and/or treating chemotherapy-induced iatrogenic pain (CIIP), the method comprising administering a therapeutically effective amount of a C5aR inhibitor to a subject undergoing chemotherapy, wherein the C5aR inhibitor is a compound of formula (II)

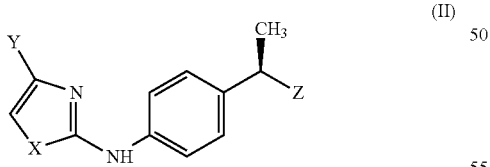

(II)

or a pharmaceutically acceptable salt thereof, wherein
X is a heteroatom selected from the group consisting of S, O and N;
Y is selected from the group consisting of:
hydrogen, halogen, linear or branched $C_1$-$C_4$-alkyl, $C_2$-$C_4$-alkenyl, $C_1$-$C_4$-alkoxy, hydroxy, —COOH, $C_1$-$C_4$-acyloxy, phenoxy, cyano, nitro, —NH$_2$, $C_1$-$C_4$-acylamino, halo-$C_1$-$C_3$-alkyl, benzoyl, linear or branched $C_1$-$C_5$-alkanesulfonate, linear or branched $C_1$-$C_5$-alkanesulfonamides, and linear or branched $C_1$-$C_8$-alkyl sulfonylmethyl;

Z is an unsubstituted tetrazole or a heteroaryl ring selected from the group consisting of:
triazole, pyrazole, oxazole, thiazole, isooxazole, isothiazole, thiadiazole and oxadiazole, wherein the heteroaryl ring is substituted by one hydroxy group, and wherein the heteroaryl ring is optionally further substituted by one or more groups selected from the group consisting of halogen, linear or branched $C_1$-$C_4$-alkyl, $C_2$-$C_4$-alkenyl, $C_1$-$C_4$-alkylamino, $C_1$-$C_4$-alkoxy, $C_1$-$C_4$-alkylthio, $C_1$-$C_4$-acyloxy, cyano, nitro, NH$_2$, $C_1$-$C_4$-acylamino, halo-$C_1$-$C_3$-alkyl, halo-$C_1$-$C_3$-alkoxy, linear or branched $C_1$-$C_5$-alkanesulfonate and linear or branched $C_1$-$C_5$-alkanesulfonamides,
and wherein the C5aR inhibitor is administered orally.

2. The method according to claim 1, wherein the chemotherapy-induced iatrogenic pain is allodynia.

3. The method according to claim 1, wherein:
X is a heteroatom selected from the group consisting of S and O;
Y is selected from the group consisting of:
hydrogen, halogen, linear or branched $C_1$-$C_4$-alkyl and halo-$C_1$-$C_3$-alkyl;
Z is an unsubstituted tetrazole or a heteroaryl ring selected from the group consisting of:
triazole, pyrazole, isooxazole, isothiazole, thiadiazole and oxadiazole, wherein the heteroaryl ring is substituted by one hydroxy group, and wherein the heteroaryl ring is optionally further substituted by one or more groups selected from the group consisting of halogen, linear or branched $C_1$-$C_4$-alkyl, $C_1$-$C_4$-alkylthio, and halo-$C_1$-$C_3$-alkyl.

4. The method according to claim 3, wherein:
Y is selected from the group consisting of hydrogen, trifluoromethyl, chlorine, methyl and t-butyl.

5. The method according to claim 3, wherein:
Z is an unsubstituted tetrazole or a heteroaryl ring selected from the group consisting of:
triazole, pyrazole, isooxazole, isothiazole, thiadiazole and oxadiazole, wherein the heteroaryl ring is substituted by one hydroxy group and wherein the heteroaryl ring is optionally further substituted by one or more groups selected from the group consisting of methyl, trifluoromethyl and chlorine.

6. The method according to claim 1, wherein the C5aR inhibitor is selected from the group consisting of:
N-{4-[(1R)-1-(1H-tetrazol-5-yl)ethyl]phenyl}-4-(trifluoromethyl)-1,3-thiazol-2-amine;
4-methyl-N-{4-[(1R)-1-(1H-tetrazol-5-yl)ethyl]phenyl}-1,3-thiazol-2-amine;
4-tert-butyl-N-{4-[(1R)-1-(1H-tetrazol-5-yl)ethyl]phenyl}-1,3-thiazol-2-amine;
N-{4-[(1R)-1-(1H-tetrazol-5-yl)ethyl]phenyl}-1,3-thiazol-2-amine;
N-{4-[(1R)-1-(1H-tetrazol-5-yl)ethyl]phenyl}-4-(trifluoromethyl)-1,3-oxazol-2-amine;
4-methyl-N-{4-[(1R)-1-(TH tetrazol-5-yl)ethyl]phenyl}-1,3-oxazol-2-amine;
5-[(1R)-1-(4-{[4-(trifluoromethyl)-1,3-thiazol-2-yl]amino}phenyl)ethyl]-1H pyrazol-1-ol;
4-methyl-5-[(1R)-1-(4-{[4-(trifluoromethyl)-1,3-thiazol-2-yl]amino}phenyl)ethyl]-1H-pyrazol-1-ol;
5-[(1R)-1-(4-([4-(trifluoromethyl)-1,3-thiazol-2-yl]amino}phenyl)ethyl]-1H-1,2,3-triazol-1-ol;
5-[(1R)-1-(4-{[4-(trifluoromethyl)-1,3-thiazol-2-yl]amino}phenyl)ethyl] isoxazol-3-ol;

4-methyl-5-[(1R)-1-(4-{[4-(trifluoromethyl)-1,3-thiazol-2-yl]amino}phenyl)ethyl]isoxazol-3-ol;

5-[(1R)-1-(4-{[4-(trifluoromethyl)-1,3-thiazol-2-yl]amino}phenyl)ethyl] isothiazol-3-ol;

4-[(1R)-1-(4-{[4-(trifluoromethyl)-1,3-thiazol-2-yl]amino}phenyl)ethyl]-1,2,5-oxadiazol-3-ol;

4-[(1R)-1-(4-{[4-(trifluoromethyl)-1,3-thiazol-2-yl]amino}phenyl)ethyl]-1,2,5-thiadiazol-3-ol; and 5-[(1R)-1-(4-{[4-(trifluoromethyl)-1,3-thiazol-2-yl]amino}phenyl)ethyl]-1H 1,2,4-triazol-1-ol.

7. The method according to claim 1, wherein the chemotherapy-induced iatrogenic pain is induced by a chemotherapeutic agent selected from the group consisting of platinum based drugs, taxanes, epothilones, plant alkaloids, thalidomide, lenalidomide and pomalidomide, carfilzomib, bortezomib and eribulin.

8. The method according to claim 7, wherein the chemotherapeutic agent is selected from the group consisting of cisplatin, carboplatin, oxaliplatin, paclitaxel, cabazitaxel, docetaxel, ixabepilone, vinblastine, vincristine, vinorelbine, etoposide, thalidomide, lenalidomide, pomalidomide, carfilzomib, bortezomib and eribulin.

9. The method according to claim 7, wherein the chemotherapeutic agent is selected from taxanes and platinum based drugs.

10. The method according to claim 8, wherein the chemotherapeutic agent is paclitaxel.

11. The method according to claim 1, wherein the C5aR inhibitor is administered as a pharmaceutical composition comprising the C5aR inhibitor and at least a pharmaceutically acceptable excipient.

* * * * *

UNITED STATES PATENT AND TRADEMARK OFFICE
CERTIFICATE OF CORRECTION

| | |
|---|---|
| PATENT NO. | : 12,102,607 B2 |
| APPLICATION NO. | : 16/769892 |
| DATED | : October 1, 2024 |
| INVENTOR(S) | : Brandolini et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 127 days.

Signed and Sealed this
Twenty-ninth Day of April, 2025

Coke Morgan Stewart
*Acting Director of the United States Patent and Trademark Office*